United States Patent [19]

Sundberg et al.

[11] Patent Number: 5,624,711
[45] Date of Patent: Apr. 29, 1997

[54] DERIVATIZATION OF SOLID SUPPORTS AND METHODS FOR OLIGOMER SYNTHESIS

[75] Inventors: Steven A. Sundberg, San Francisco; David Fujimoto, Mountain View, both of Calif.

[73] Assignee: Affymax Technologies, N.V., Curacao, Netherlands

[21] Appl. No.: 431,196

[22] Filed: Apr. 27, 1995

[51] Int. Cl.$^6$ ........................................... B05D 1/36
[52] U.S. Cl. .................... 427/261; 427/287; 427/387; 427/407.2; 422/134; 436/518; 436/527; 436/532; 435/4; 435/7.1; 530/334; 530/335; 530/337
[58] Field of Search ............... 436/518, 524–535; 530/333, 334, 335, 336, 337; 435/4, 7.1; 422/131, 134; 427/407.2, 387, 261, 287

[56] References Cited

U.S. PATENT DOCUMENTS

| | | |
|---|---|---|
| 4,593,029 | 6/1986 | Venuti et al. . |
| 4,619,970 | 10/1986 | Okamoto et al. .................... 525/100 |
| 4,728,502 | 3/1988 | Hamill . |
| 4,812,512 | 3/1989 | Buendia et al. .................... 525/54.11 |
| 5,143,854 | 9/1992 | Pirrung et al. .................... 436/518 |
| 5,288,514 | 2/1994 | Ellman . |
| 5,324,633 | 6/1994 | Fodor et al. . |
| 5,451,683 | 9/1995 | Barrett et al. .................... 548/302.7 |

FOREIGN PATENT DOCUMENTS

| | | |
|---|---|---|
| WO90/00626 | 1/1990 | WIPO . |
| 9009238 | 8/1990 | WIPO . |
| WO90/15070 | 12/1990 | WIPO . |
| WO92/10092 | 6/1992 | WIPO . |
| WO93/04145 | 3/1993 | WIPO . |
| WO93/10183 | 5/1993 | WIPO . |
| WO93/10162 | 5/1993 | WIPO . |
| WO95/04160 | 2/1995 | WIPO . |

OTHER PUBLICATIONS

Surrey, A.R., et al., *J. Am. Chem. Soc.*, 80:3469–3471 (1958).
Fenech, G., et al., *Gazz. Chim. Ital.*, 91:163–172 (1961).
Nagakura, I., et al., *Heterocycles*, 3(6):453–457 (1975).
Rich, D.H., et al., *J. Am. Chem. Soc.*, 97:1575–1579 (1975).
Barany, G., et al., *J. Am. Chem. Soc.*, 107:4936–4942 (1985).
Wang, S.S., *J. Org. Chem.*, 41(20):3258–3261 (1976).
Bellof, D., et al., *Chimia*, 39(10):317–320 (1985).
Abraham, N.A., et al., *Tetrahedron Letters*, 32(5):577–580 (1991).
Cook, R.M., et al., *Tetrahedron Letters*, 35(37):6777–6780 (1994).
Geysen, et al., *J. Immun. Meth.*, 102:259–274 (1987).
Frank, et al. *Tetrahedron*, 44:6031–6040 (1988).
Fodor, et al., *Science*, 251:767–773 (1991).
Bush, et al., *Amer. J. Optometry Physiol. Optics*, 65(9):722–728 (1988).
Green, M., et al., *Adv. Protein Chem.*, 29:85–133 (1975).
Greene, T.W., et al., *Protective Groups in Organic Synthesis*, published 1991 by John Wiley (N.Y.), pp. 1–362, see pp. 27, 62, 88, 89, 315, 349 and 362.
Dugave, C., et al., "Synthesis of Activated Disulfide Adducts Containing a 4–Diazocyclohexa–2,5–dienone Precursor for Photoaffinity Labelling," *Tetrahedron Letters*, 35(51):9557–9560, (1994).

(List continued on next page.)

*Primary Examiner*—Shrive Beck
*Assistant Examiner*—Erma Cameron
*Attorney, Agent, or Firm*—Townsend and Townsend and Crew

[57] ABSTRACT

Methods and derivatized supports which are useful in solid-phase synthesis of peptides, oligonucleotides or other small organic molecules as well as arrays of ligands. The methods provide means to control the functional site density on a solid support. Some of the derivatized supports are polymer-coated or glycan-coated. Other methods for regenerating the surface of a used ligand array are also provided.

8 Claims, 17 Drawing Sheets

OTHER PUBLICATIONS

Rajasekharan Pillai, V.N., et al., "New, Easily Removable Poly(ethylene glycol) Supports for the Liquid-Phase Method of Peptide Synthesis," *J. Org. Chem.*, 45(26):5364–5370 (1980).

Jones, G.H., et al., "Inhibitors of Cyclic AMP Phosphodiesterase: 1. Analogs of cilostamide and anagrelide," *Chemical Abstracts*, 106(13):102224 (1987); *J. Medical Chemistry*, 30(2):295–303 (1987) see compounds: 105763–67–5, 105763–74–4, 105763–73–3 and 105763–76–6.

Timofeev, E.N., et al., "Chemical Design in Gel–Based Shom," International Workshop on Sequencing by Hybridization, hosted by Houston Advanced Research Center DNA Technology Laboratory, Oct. 29–30, 1993.

Cass, R., et al., *Peptides: Chemistry, Structure and Biology*, 975–977 (Jun. 20–25, 1993).

Lofas, S. et al., *J. Chem. Soc., Chem. Commun.*, 1526–1528 (1990).

Marengere, L.E.M., et al., *Nature*, 502–505 (9 Jun. 1994).

Payne, G., et al., *Proc. Natl. Acad. Sci. USA*, 4902–4906 (Jun. 1993).

Fodor, S.P.A., et al., *Nature*, 364:555–556 (5 Aug. 1993).

Dower, et al., *Ann. Rep. Med. Chem.*, 28:271–280 (1991).

Holmes, et al., "New Techniques in Random Screening," 12th Int'l Symp. on Medicinal Chemistry, Basel, Switzerland (13–17 Sep. 1992).

Polyethyleneimine: $(-CH_2-CH_2-NH_x-)_n$
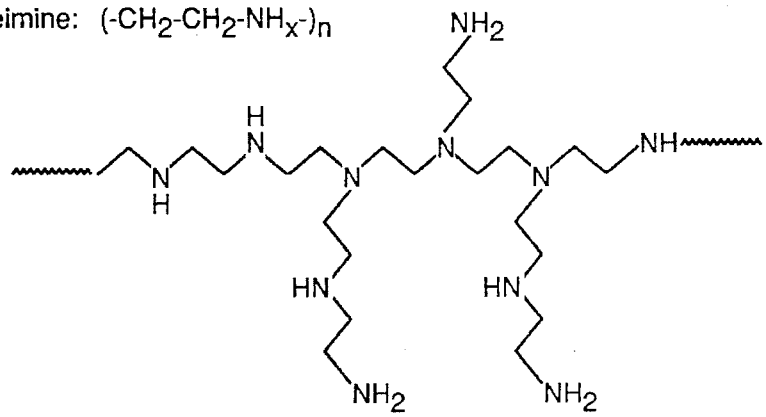
Polyacrylamide: $(-CH_2-CH-)_n$
            |
            $CONH_2$
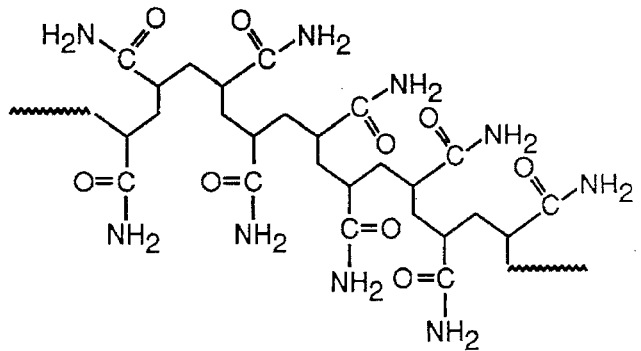
Polyallylamine: $(-CH_2-CH-)_n$
             |
             $CH_2-NH_2$
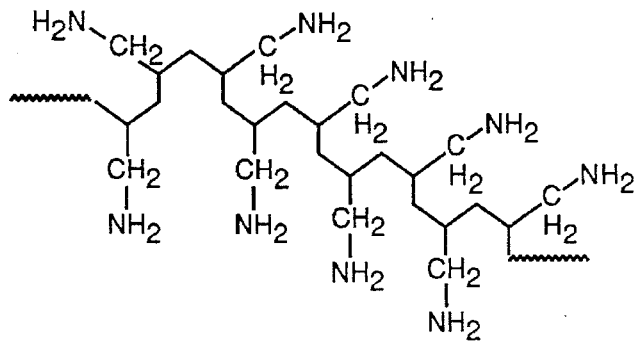
Figure 3

Polymer Structures
Poly(acrylic acid): (-CH$_2$-CH-)$_n$
                          |
                        COOH
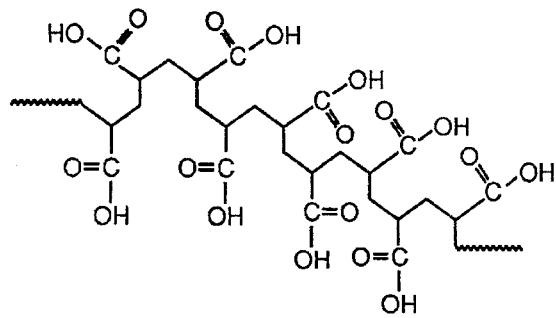
Poly(ethylene/maleic anhydride): (-CH$_2$-CH$_2$-CH-CH-)$_n$
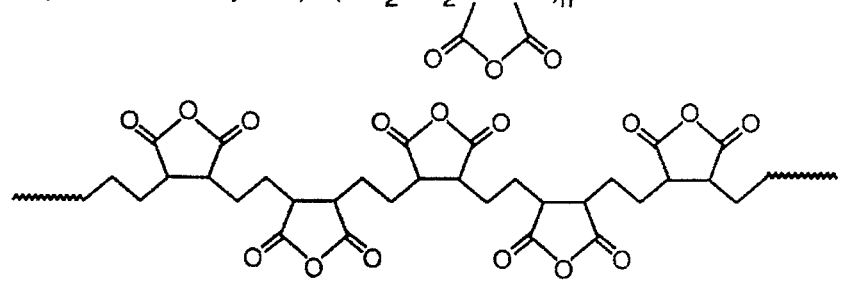
Poly(methylvinylether/maleic anhydride): (-CH$_2$-CH-CH-CH-)$_n$
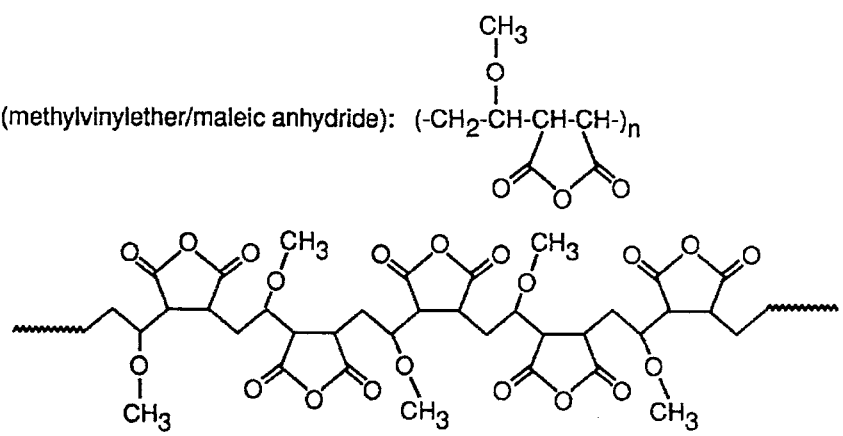
Figure 4

Polymer Structures
Polyethylene glycol: HO-CH$_2$-CH$_2$-(O-CH$_2$-CH$_2$)$_n$-O-CH$_2$-CH$_2$-OH
Poly(vinyl alcohol): (-CH-CH-)$_n$
              |   |
              OH OH
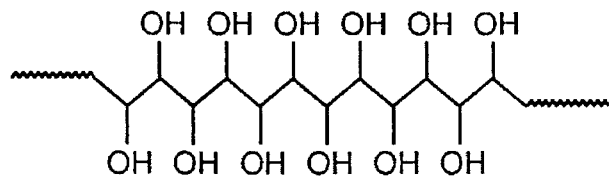
Figure 5

Polymer/Glass Compsites

Polymer Cross-linking to Form Networks

Polymer Cross-linking to Aminopropylated Glass

Polymer Cross-linking to Epoxy Silanated Glass

Contact angle data for substrates prepared using different linkers

Discrimination between specific and non-specific binding

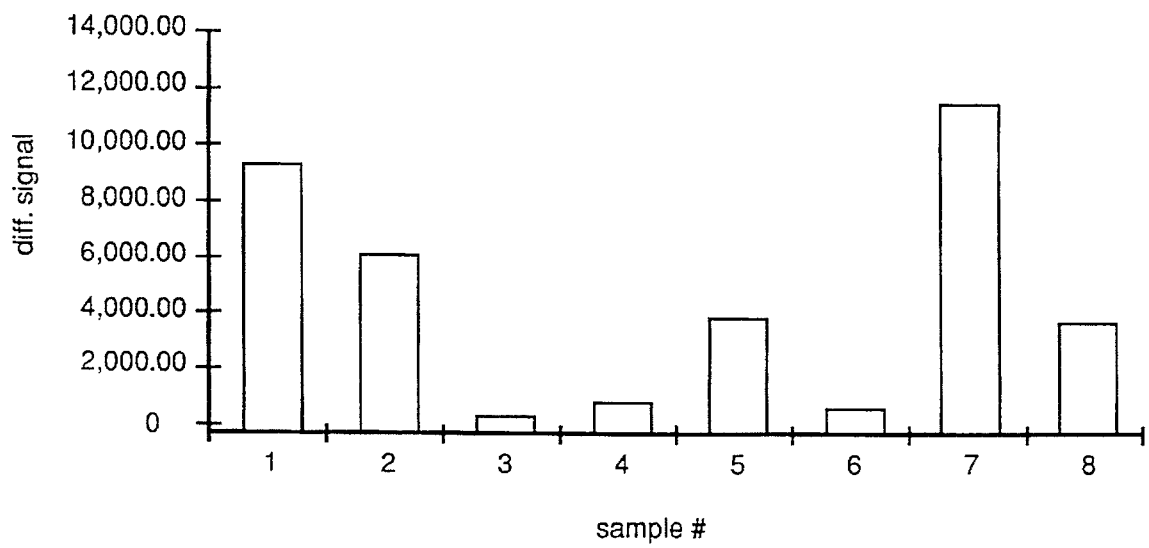

Surface 1 = 100% aminocaproic
2 = 100% trigly
3 = 10% aminocaproic/N-acetylated glycine
4 = 10% trigly/N-acetylated glycine
5 = 10% aminocaproic/N-acetylated serine
6 = standard aminocaproic
7 = 100% 15-atom-PEG
8 = 10% 15-atom-PEG/N-actylated glycine Rank Order Consensus (2 experiments):
100% 15-atom-PEG   (best)
100% trigly
10% aminocaproic/N-acetylated serine
standard aminocaproic
10% aminocaproic/N-acetylated glycine   (worst)

Figure 15

Oligonucleotide Synthesis

Peptide Synthesis

DERIVATIZATION OF SOLID SUPPORTS AND METHODS FOR OLIGOMER SYNTHESIS

BACKGROUND OF THE INVENTION

The present invention relates to the field of solid phase polymer synthesis. More specifically, the invention provides methods and derivatized supports which find application in solid phase synthesis of oligomer arrays or of single compounds on a preparative scale. The oligomer arrays which are prepared using the derivatized supports of the present invention may be used, for example, in screening studies for determination of binding affinity and in diagnostic applications.

The synthesis of biological polymers such as peptides and oligonucleotides has been evolving in dramatic fashion from the earliest stages of solution synthesis to solid phase synthesis of a single polymer to the more recent preparations of libraries having large numbers of diverse oligonucleotide sequences on a single solid support or chip.

Improved methods of forming large arrays of oligonucleotides, peptides and other polymer sequences in a short period of time have been devised. Of particular note, Pirrung et al., U.S. Pat. No. 5,143,854 (see also PCT Application No. WO 90/15070) and Fodor et al., PCT Publication No. WO 92/10092, all incorporated herein by reference, disclose methods of forming vast arrays of peptides, oligonucleotides and other polymer sequences using, for example, light-directed synthesis techniques. See also, Fodor et al., Science, 251:767–777 (1991), also incorporated herein by reference for all purposes. These procedures are now referred to as VLSIPS™ procedures.

In the above-referenced Fodor et al., PCT application, an elegant method is described for using a computer-controlled system to direct a VLSIPS™ procedure. Using this approach, one heterogenous array of polymers is converted, through simultaneous coupling at a number of reaction sites, into a different heterogenous array. See, application Ser. Nos. 07/796,243 and 07/980,523, the disclosures of which are incorporated herein for all purposes.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to provide a partial or complete sequence of a target nucleic acid and to detect the presence of a nucleic acid containing a specific oligonucleotide sequence.

The control of surface properties to optimize VLSIPS™ substrate performance in both chemical synthesis and bioassays has been recognized to involve such parameters as site density for synthesis initiation, surface wettability and the length of the linking group which attaches the initiation site to the surface. Additionally, alternative surfaces can lead to the use of VLSIPS™ technology for preparative scale synthesis.

SUMMARY OF THE INVENTION

The present invention provides a variety of derivatized supports and methods for their preparation, which are useful in the preparation of peptides, oligonucleotides or other small organic molecules.

Some of the methods involve substrate surface derivatization in a manner which also expands the types of synthesis which can be performed and provides lower density arrays of polymers for use in diagnostics.

A number of novel derivatized supports are provided which have altered surfaces, for example polymer-coated or glycan-coated solid supports. Other derivatized supports utilize linking groups terminating in acidic functionalities such as carboxylic acids or sulfonic acids which are useful in alternative synthesis strategies.

The present invention further provides methods of rendering the derivatized supports reusable.

The present invention still further provides methods of oligomer synthesis.

Thus, according to a first aspect of the invention, a substrate surface, useful for the preparation of diverse polymer sequences is derivatized to control functional group spacing, improve wettability, and minimize non-specific binding of macromolecules. In one embodiment, the substrate surface is first derivatized with a trialkoxysilane bearing a reactive site such as amino ($-NH_2$), isothiocyanate ($-NCS$) or hydroxyl ($-OH$) for the attachment of a suitable linking group. Mixtures of suitably protected linking groups having synthesis initiation sites and an "inert" diluent (or capping agent) are then reacted with the derivatized surface to provide a substrate surface wherein the average spacing of synthesis initiation sites is altered. This method provides effective control of functional site density and can be adapted to control other surface properties such as surface wettability and nonspecific binding of macromolecules.

In another aspect, the present invention provides methods for the preparation of stabilized polymer-coated supports for use in solid-phase synthesis. These methods typically use dip coating, covalent polymer attachment, in situ polymerization, or combinations thereof to provide the polymer-coated support.

In yet another aspect, the present invention provides glycan-coated supports and methods for their preparation. While similar to the polymer-coated supports, the properties of glycan-coated supports can be quite different and provide extremely hydrophilic surfaces which are useful in binding assays and diagnostic applications.

In still another aspect, the present invention provides methods for the surface-regeneration of used ligand arrays.

BRIEF DESCRIPTION OF THE DRAWINGS

FIG. 3 provides the structures of three polymers (polyethyleneimine, polyacrylamide and polyallylamine) which are useful for preparing polymer-coated glass substrates.

FIG. 4 provides the structures of a group of carboxylic acid and anhydride polymers which are useful for the preparation of polymer-coated solid supports.

FIG. 5 provides the structures of polyethylene glycol and poly(vinyl alcohol) which are useful for preparing polymer-coated solid supports.

FIG. 15 is a graph which illustrates the discrimination between specific and non-specific binding observed in a streptavidin/biotin binding assay as a function of surface preparation.

DETAILED DESCRIPTION OF THE INVENTION

Contents

Figure 1:
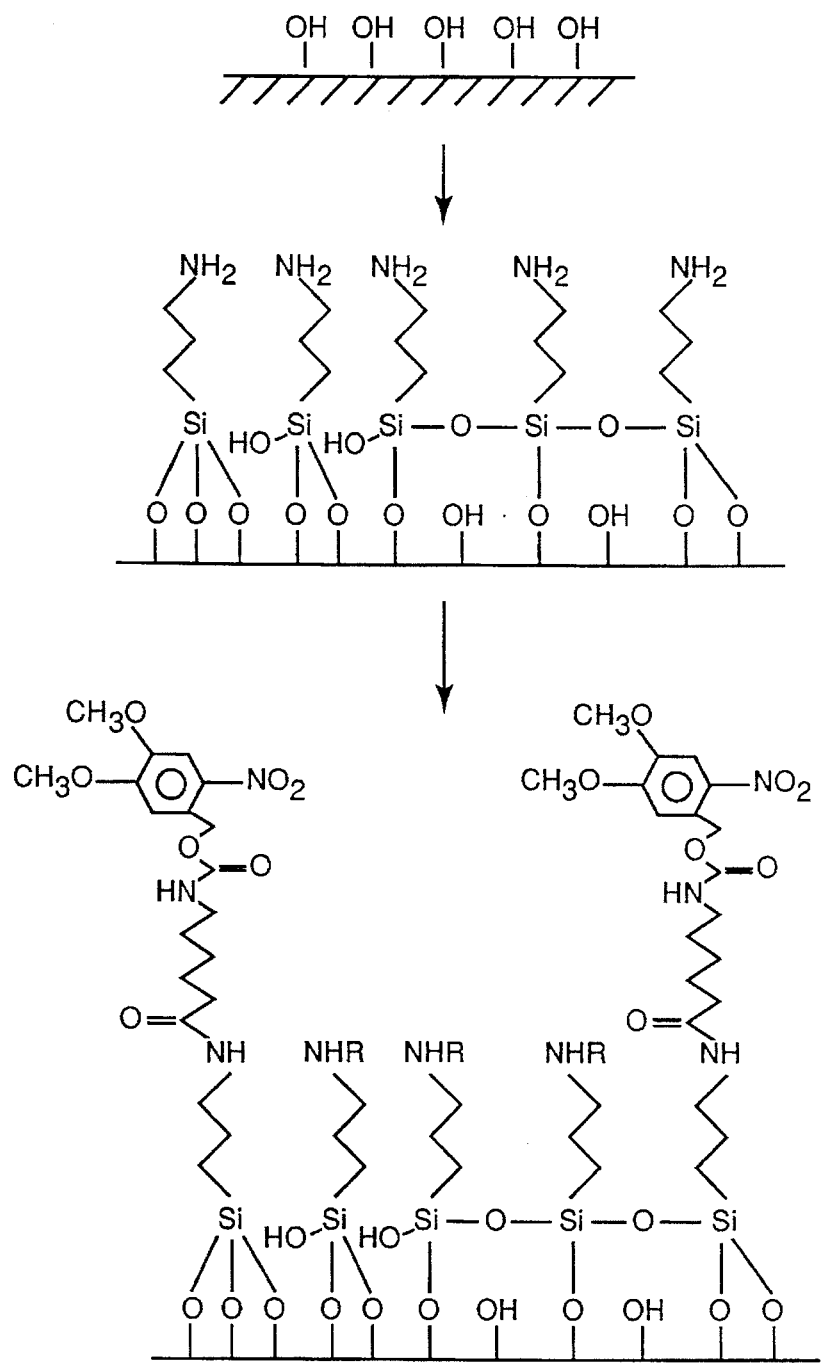
FIG. 1 illustrates a doped process of substrate derivatization.

I. Glossary
II. General
III. Surface Engineering—The Doped Process
IV. Carboxy Chips
V. Polymer-Coated Surfaces
VI. Glycan-Coated Chips
VII. Reusable Chips
VIII. Methods for Oligomer Synthesis
IX. Examples
X. Conclusion

I. Glossary

The following abbreviations are used herein: AcOH, acetic acid; ALLOC, allyloxycarbonyl; BOP, benzotriazol-1-yloxy-tris(dimethylamino)phosphonium hexafluorophosphate; CAP, ε-aminocaproic acid; DIEA, diisopropylethylamine; DIGLY, glycylglycine; DMF, dimethylformamide; DMT, dimethoxytrityl; DTT, dithiothreitol; EtOAc, ethyl acetate; FMOC, fluorenylmethoxycarbonyl; MeNPOC, α-methylnitropiperonyloxycarbonyl; MP, melting point; NVOC, nitroveratryloxycarbonyl; OBt, hydroxybenzotriazole radical; PBS, phosphate buffered saline; TFA, trifluoroacetic acid; 15-ATOM-PEG, $H_2N-(CH_2CH_2O)_2-CH_2CH_2NHCO-(CH_2)_3-CO_2H$; TRIGLY, glycylglycylglycine.

The following terms are intended to have the following general meanings as they are used herein:

Chemical terms: As used herein, the term "alkyl" refers to a saturated hydrocarbon radical which may be straight-chain or branched-chain (for example, ethyl, isopropyl, t-amyl, or 2,5-dimethylhexyl). When "alkyl" or "alkylene" is used to refer to a linking group or a spacer, it is taken to be a group having two available valences for covalent attachment, for example, $-CH_2CH_2-$, $-CH_2CH_2CH_2-$, $-CH_2CH_2CH(CH_3)CH_2-$ and $-CH_2(CH_2CH_2)_2CH_2-$. Preferred alkyl groups as substituents are those containing 1 to 10 carbon atoms, with those containing 1 to 6 carbon atoms being particularly preferred. Preferred alkyl or alkylene groups as linking groups are those containing 1 to 20 carbon atoms, with those containing 3 to 6 carbon atoms being particularly preferred. The term "polyethylene glycol" is used to refer to those molecules which have repeating units of ethylene glycol, for example, hexaethylene glycol ($HO-(CH_2CH_2O)_5-CH_2CH_2OH$). When the term "polyethylene glycol" is used to refer to linking groups and spacer groups, it would be understood by one of skill in the art that other polyethers or polyols could be used as well (i.e., polypropylene glycol or mixtures of ethylene and propylene glycols).

The term "protecting group" as used herein, refers to any of the groups which are designed to block one reactive site in a molecule while a chemical reaction is carried out at another reactive site. More particularly, the protecting groups used herein can be any of those groups described in Greene, et al., *Protective Groups In Organic Chemistry*, 2nd Ed., John Wiley & Sons, New York, N.Y., 1991, incorporated herein by reference. The proper selection of protecting groups for a particular synthesis will be governed by the overall methods employed in the synthesis. For example, in "light-directed" synthesis, discussed below, the protecting groups will be photolabile protecting groups such as dimethoxybenzoin, NVOC, MeNPOC, and those disclosed in co-pending Application PCT/US93/10162 (filed Oct. 22, 1993), incorporated herein by reference. In other methods, protecting groups may be removed by chemical methods and include groups such as FMOC, DMT and others known to those of skill in the art.

The term "protected amino acid" refers to an amino acid, typically an α-amino acid having either or both the amine functionality and the carboxylic acid functionality suitably protected by one of the groups described above. Additionally, for those amino acids having reactive sites or functional groups on a side chain (i.e., serine, tyrosine, glutamic acid), the term "protected amino acid" is meant to refer to those compounds which optionally have the side chain functionality protected as well.

The term "activating agent" refers to those groups which, when attached to a particular functional group or reactive site, render that site more reactive toward covalent bond formation with a second functional group or reactive site. For example, the group of activating groups which are useful for a carboxylic acid include simple ester groups and anhydrides. The ester groups include alkyl, aryl and alkenyl esters and in particular such groups as 4-nitrophenyl, N-hydroxylsuccinimide and pentafluorophenol. Other activating agents are known to those of skill in the art.

Ligand: A ligand is a molecule that is recognized by a receptor. Examples of ligands which can be synthesized using the methods and compounds of this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

Monomer: A monomer is a member of the set of small molecules which are or can be joined together to form a polymer or a compound composed of two or more members. The present invention is described herein in terms of compositions and methods which are useful in solid phase synthesis. In a number of applications, solid phase methods are used for the preparation of biological polymers such as peptides, proteins and nucleic acids. For these biological polymers, the set of monomers includes but is not restricted to, for example, the set of common L-amino acids, the set of D-amino acids, the set of synthetic and/or natural amino acids, the set of nucleotides and the set of pentoses and hexoses. The particular ordering of monomers within a biological polymer is referred to herein as the "sequence" of the polymer. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either $\alpha$-, $\beta$-, or $\omega$-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in copending application U.S. Ser. No. 08/351,058 which is a CIP of U.S. Ser. No. 07/978,940 which is a CIP of U.S. Pat. No. 5,242,974, entitled "POLYMER REVERSAL ON SOLID SURFACES," incorporated herein by reference for all purposes.

In certain embodiments of the invention, polymer-coated supports are described. The polymers used for coating a solid support include, but are not limited to polyurethanes, polyesters, polycarbonates, polyureas, polyamides, polyethyleneimines, polyarylene sulfides, polysiloxanes, polyacrylamides, polyimides, polyacetates, or other polymers which will be apparent upon review of this disclosure. The polymers used to coat a solid support are typically repeats of a single monomers which is crosslinked with a second molecule to provide structural integrity to the polymer.

Peptide: A peptide is a polymer in which the monomers are amino acids and are joined together through amide bonds, alternatively referred to as a polypeptide. When the amino acids are $\alpha$-amino acids, either the L-optical isomer or the D-optical isomer may be used. Additionally, unnatural amino acids, for example, $\beta$-alanine, phenylglycine and homoarginine are also meant to be included. Peptides are two or more amino acid monomers long and are often more than 20 amino acid monomers long. Standard abbreviations for amino acids are used (e.g., P for proline). These abbreviations are included in Stryer, *Biochemistry*, Third Ed., 1988, which is incorporated herein by reference for all purposes.

Receptor: A receptor is a molecule that has an affinity for a ligand. Receptors may be naturally-occurring or manmade molecules. They can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as anti-ligands. As the term receptors is used herein, no difference in meaning is intended. A "Ligand Receptor Pair" is formed when two molecules have combined through molecular recognition to form a complex.

Substrate: As used herein, the term "substrate" or "support" refers to a material having a rigid or semi-rigid surface.

In many embodiments, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other embodiments, small beads may be provided on the surface, and compounds synthesized thereon may be released upon completion of the synthesis.

Channel Block: A material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

Predefined Region: A predefined region is a localized area on a substrate which is, was, or is intended to be used for formation of a selected polymer and is otherwise referred to herein in the alternative as "reaction" region, a "selected" region, or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 cm$^2$, more preferably less than 1 mm$^2$, and still more preferably less than 0.5 mm$^2$. In most preferred embodiments the regions have an area less than about 10,000 $\mu$m$^2$ or, more preferably, less than 100 $\mu$m$^2$. Within these regions, the polymer synthesized therein is preferably synthesized in a substantially pure form. Additionally, multiple copies of the polymer will typically be synthesized within any preselected region. The number of copies can be in the thousands to the millions.

II. General

The compounds, compositions and methods of the present invention can be used in a number of solid phase synthesis applications, including light-directed methods, flow channel and spotting methods, pin-based methods and bead-based methods.

Light-Directed Methods

"Light-directed" methods (which are one technique in a family of methods known as VLSIPS™ methods) are described in U.S. Pat. No. 5,143,854, previously incorporated by reference. The light directed methods discussed in the '854 patent involve activating predefined regions of a substrate or solid support and then contacting the substrate with a preselected monomer solution. The predefined regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

Flow Channel or Spotting Methods

Additional methods applicable to library synthesis on a single substrate are described in co-pending applications Ser. Nos. 07/980,523, filed Nov. 20, 1992, and 07/796,243, filed Nov. 22, 1991, incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously.

Pin-Based Methods

Another method which is useful for the preparation of compounds and libraries of the present invention involves "pin based synthesis." This method is described in detail in U.S. Pat. No. 5,288,514, previously incorporated herein by reference. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of oligonucleotides, for example, the spacer may be selected from a wide variety of molecules which can be used in organic environments associated with synthesis as well as aqueous environments associated with binding studies. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., *Solid Phase Peptide Synthesis*, IRL Press (1989), incorporated herein by reference. In some embodiments, the spacer may provide for a cleavable function by way of, for example, exposure to acid or base.

Bead Based Methods

Yet another method which is useful for synthesis of polymers and small ligand molecules on a solid support "bead based synthesis." A general approach for bead based synthesis is described copending application Serial Nos. 07/762,522 (filed Sep. 18, 1991); 07/946,239 (filed Sep. 16, 1992); 08/146,886 (filed Nov. 2, 1993); 07/876,792 (filed Apr. 29, 1992); PCT/US94/12347 (filed Nov. 2, 1994) and PCT/US93/04145 (filed Apr. 28, 1993), the disclosures of which are incorporated herein by reference.

For the synthesis of molecules such as oligonucleotides on beads, a large plurality of beads are suspended in a suitable carrier (such as water) in a container. The beads are provided with optional spacer molecules having an active site. The active site is protected by an optional protecting group.

In a first step of the synthesis, the beads are divided for coupling into a plurality of containers. For the purposes of this brief description, the number of containers will be limited to three, and the monomers denoted as A, B, C, D, E, and F. The protecting groups are then removed and a first portion of the molecule to be synthesized is added to each of the three containers (i.e., A is added to container 1, B is added to container 2 and C is added to container 3).

Thereafter, the various beads are appropriately washed of excess reagents, and remixed in one container. Again, it will be recognized that by virtue of the large number of beads utilized at the outset, there will similarly be a large number of beads randomly dispersed in the container, each having a particular first portion of the monomer to be synthesized on a surface thereof.

Thereafter, the various beads are again divided for coupling in another group of three containers. The beads in the first container are deprotected and exposed to a second monomer (D), while the beads in the second and third containers are coupled to molecule portions E and F respectively. Accordingly, molecules AD, BD, and CD will be present in the first container, while AE, BE, and CE will be present in the second container, and molecules AF, BF, and CF will be present in the third container. Each bead, however, will have only a single type of molecule on its surface. Thus, all of the possible molecules formed from the first portions A, B, C, and the second portions D, E, and F have been formed.

The beads are then recombined into one container and additional steps such as are conducted to complete the synthesis of the polymer molecules. In a preferred embodiment, the beads are tagged with an identifying tag which is unique to the particular double-stranded oligonucleotide or probe which is present on each bead. A complete description of identifier tags for use in synthetic libraries is provided in copending application Ser. No. 08/146,886 (filed Nov. 2, 1993) previously incorporated by reference for all purposes.

The advent of methods for the synthesis of diverse chemical compounds on solid supports has resulted in the genesis of a multitude of diagnostic applications for such chemical libraries. A number of these diagnostic applications involve contacting a sample with a solid support, or chip, having multiple attached biological polymers such as peptides and oligonucleotides, or other small ligand molecules synthesized from building blocks in a stepwise fashion, in order to identify any species which specifically binds to one or more of the attached polymers or small ligand molecules.

For example, patent application Ser. No. 08/082,937, filed Jun. 25, 1993, describes methods for making arrays of oligonucleotide probes that can be used to provide the complete sequence of a target nucleic acid and to detect the presence of a nucleic acid containing a specific oligonucleotide sequence. Patent application Ser. No. 08/327,687, filed Oct. 24, 1994, describes methods of making arrays of unimolecular, double-stranded oligonucleotides which can be used in diagnostic applications involving protein/DNA binding interactions such as those associated with the p53 protein and the genes contributing to a number of cancer conditions. Arrays of double-stranded oligonucleotides can also be used to screen for new drugs having particular binding affinities.

A number of factors contribute to the successful synthesis and use of oligomer arrays on solid supports. For example, issues of relevance to the use of derivatized glass substrates for carrying out VLSIPS™ synthesis of peptide arrays are the spacing of the synthesis initiation sites, the wettability of the surface by organic solvents and aqueous solutions, and the extent to which non-specific binding of receptors, antibodies or other biological macromolecules occurs.

The spacing of the synthesis initiation sites (typically, primary amines) is of concern since very high site densities will affect binding events between tethered ligands and receptors. Additionally, increased yields in synthesis can be achieved by control of phenomena such as free radical formation during photolytic reaction, solvent accessibility and surface electrostatic effects.

It will be apparent to those of skill in the art that the methods and compositions of the present invention will find application in any of the above-noted processes for solid phase synthesis of biological polymers and other small molecule ligands. Additionally, the method of regenerating a used ligand array surface will find application with ligand arrays prepared by light-directed methods, bead- or pin-based methods, or flow channel or spotting methods.

III. Surface Engineering—The Doped Process

The derivatization of supports for the preparation of ligand arrays, as well as other forms of solid phase synthesis, must take into account several issues relating to both the synthesis which occurs on the support and the subsequent use of the arrays in binding studies and diagnostic assays. Foremost among the many issues are the spacing of initiation sites, the wettability of the surface by both organic solvents and aqueous solutions, and the extent to which non-specific binding of receptors occurs.

The spacing of synthesis initiation sites on a solid support can affect not only the synthesis of the ligand array but also the binding events between a receptor and a tethered ligand. The synthesis can be influenced through phenomena such as free radical formation during photolytic reaction (in light-directed synthesis), solvent accessibility and surface electrostatic effects.

The wettability of the support, or substrate surface, is also likely to have a direct influence on the yield of coupling reactions and subsequent binding events. The presentation of peptides or other ligands for recognition is expected to be a function of not only the hydrophobicity/hydrophilicity of the peptide or ligand, but also the physicochemical nature of the surface to which it is attached. Thus, hydrophilic peptide sequences are expected to extend fully into the surrounding aqueous environment, thereby maximizing their availability for recognition and binding by receptors. In contrast, hydrophobic sequences in the presence of a moderately hydrophobic substrate surface can collapse onto the surface and effectively be eliminated from the pool of available ligands presented to a receptor.

In view of the above considerations, the present invention provides a method for affixing functional sites to the surface of a solid substrate at a preselected density. In this method, a solid substrate is reacted with a derivatization reagent having a substrate attaching group on one end and a reactive site on a distal end (away from the surface) to provide a substrate having an even distribution of reactive sites. The derivatized substrate is then contacted with a mixture of linking molecules and diluent molecules. The linking molecules each have reactive groups which are capable of covalent attachment to the reactive sites on the derivatized substrate. The linking molecules additionally have a functional group which is optionally protected. The ratio of the linking molecules to the diluent molecules in the mixture is selected to control the functional site density on the surface of the substrate. The contact is carried out for a sufficient period of time to bind the linking molecules and the diluent molecules to the substrate.

The broad concept of this aspect of the invention is provided in FIG. 1 which illustrates the "doped process" of derivatizing a solid support. A related method, termed the "standard process," is provided for comparison in FIG. 2. In the doped process, a support (for example, a glass slide) is cleaned and derivatized with an aminoalkylsilane to provide a surface of amine functional groups. Treatment of this derivatized substrate with a mixture of linking molecules (for example, NVOC-aminocaproic acid) and diluent molecules (for example, protected amino acids) provides a surface having synthesis initiation sites at a preselected density. The density of synthesis initiation sites will depend on the particular ratio of linking molecules to diluent molecules which is used.

The solid substrate may be biological, nonbiological, organic, inorganic, or a combination of any of these, existing as particles, strands, precipitates, gels, sheets, tubing, spheres, containers, capillaries, pads, slices, films, plates, slides, etc. The solid substrate is preferably flat but may take on alternative surface configurations. For example, the solid substrate may contain raised or depressed regions on which synthesis takes place. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid substrate materials will be readily apparent to those of skill in the art. Preferably, the surface of the solid substrate will contain reactive groups, which could be carboxyl, amino, hydroxyl, thiol, or the like. More preferably, the surface will be optically transparent and will have surface Si—OH functionalities, such as are found on silica surfaces.

The derivatization reagent can be attached to the solid substrate via carbon—carbon bonds using, for example, substrates having (poly)trifluorochloroethylene surfaces, or more preferably, by siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups.

The particular derivatization reagent used can be selected based upon its hydrophilic/hydrophobic properties to improve presentation of an attached oligomer to certain receptors, proteins or drugs. As noted above, the derivatization reagent, prior to attachment to the solid substrate, has a substrate attaching group at one end, and a reactive site at the other end. The reactive site will be a group which is appropriate for attachment to a linking molecule or a diluent molecule. For example, groups appropriate for attachment to a silica surface would include trichlorosilyl and trialkoxysilyl functional groups. Groups which are suitable for attachment to a linking molecule or diluent molecule include amine, hydroxyl, thiol, carboxylic acid, ester, amide, epoxide, isocyanate and isothiocyanate. Additionally, for use in synthesis, the derivatization reagents used herein will typically have a protecting group attached to the reactive site on the distal or terminal end of the derivatization reagent (opposite the solid substrate). Preferred derivatization reagents include aminoalkyltrialkoxysilanes, aminoalkyltrichlorosilanes, hydroxyalkyltrialkoxysilanes, hydroxyalkyltrichlorosilanes, carboxyalkyltrialkoxysilanes, polyethyleneglycols, epoxyalkyltrialkoxysilanes, and combinations thereof.

After derivatization of the substrate, the derivatized surface is contacted with a mixture of linking molecules and diluent molecules. The diluent molecules have only one center which is reactive with the reactive sites on the derivatized substrate surface. All the other reactive centers on the diluent molecules are protected, capped or otherwise rendered inert. The linking molecules will similarly have one center which is reactive with the reactive sites on the derivatized substrate surface. Additionally, the linking molecules will have a functional group which is optionally protected and which can later serve as a synthesis initiation site. The linking and diluent molecules are present in the mixture in a ratio which is selected to control the functional site density on the surface. The ratio of linking molecules to diluent molecules is typically from about 1:2 to about 1:200, and preferably from about 1:10 to about 1:50.

The linking molecules used in the present invention are preferably of sufficient length to permit any polymers synthesized thereon to interact freely with molecules exposed to the polymers. The linking molecules should be 3–50 atoms long to provide sufficient exposure of ligands to their receptors. Typically, the linking molecules will be aryl acetylene, ethylene glycol oligomers containing 2–14 monomer units, diamines, diacids, amino acids, peptides, or combinations thereof. In some embodiments, the linking molecule can be a polynucleotide. The particular linking molecule used can be selected based upon its hydrophilic/hydrophobic properties to improve presentation of the polymer synthesized thereon to certain receptors, proteins or drugs. As noted above, the linking molecule, prior to attachment to the derivatized surface has an appropriate functional group at each end, one group appropriate for attachment to the reactive sites on a derivatized surface and the other group appropriate as a synthesis initiation site. For example, groups appropriate for attachment to the derivatized surface would include amino, hydroxy, thiol, carboxylic acid, ester, amide, isocyanate and isothiocyanate. Additionally, for subsequent use in synthesis of polymer arrays or libraries, the linking molecules used herein will typically have a protecting group attached to the functional group on the distal or terminal end of the linking molecule (opposite the solid support).

The linking molecule contributes to the net hydrophobic or hydrophilic nature of the surface. For example, when the linking molecules comprise a hydrocarbon chain, such as —$(CH_2)_n$—, the effect is to decrease wettability. Linking molecules including polyoxyethylene (—$(CH_2CH_2O)_n$—), or polyamide (—$(CH_2CONH)_n$—) chains tend to make the surface more hydrophilic (i.e., increase wettability).

The diluent molecules can be any of a variety of molecules which can react with the reactive sites present on the derivatized substrate and which have any remaining functional groups capped or protected. The diluent molecules can also be selected to impart hydrophobic or hydrophilic properties to the substrate surface. For example, in one embodiment the diluent molecules are alkanoic acids, which impart hydrophobic properties to the surface. In other embodiments, the diluent molecules are amino acids, wherein the amine and any side chain functionality which is present are protected. In these embodiments, the diluent molecules can contain functionality which is altered upon treatment with various reagents such as acid, base or light, to generate a surface having other desired properties. For example, use of O-t-Butyl serine as a diluent molecule provides a hydrophobic surface during polymer synthesis, but upon treatment with acid (cleaving the t-butyl ether), a more hydrophilic surface is produced for assays. Thus, after reacting the mixture of linking molecules and diluent molecules with the surface and subsequently synthesizing a desired polymer onto the functional sites on the linking group, the protecting groups on the surface-attached diluent molecules are removed to provide a more hydrophilic (i.e. "wettable") surface. In preferred embodiments, the diluent molecules are protected glycine, protected serine, glutamic acid or protected lysine.

The protecting groups which are used in certain embodiments of the invention are selected so as to be selectively removable. Examples of suitable protecting groups are FMOC, DMT, NVOC, MeNPOC, BOC and ALLOC.

IV. Carboxy Chips

The present invention also provides solid supports which are derivatized to provide acidic surfaces, or "carboxy chips." The carboxy chips can be considered as "reverse polarity" surfaces (as compared with the more typical aminopropylsilane derivatized surfaces). Such reverse polarity surfaces will find application in combinatorial synthesis strategies which require a carboxylic acid initiation site. For example, peptide synthesis which is carried out from the N-terminal end to the C-terminal end can be carried out on a carboxy chip. Additionally, small molecules such as prostaglandins, β-turn mimetics and benzodiazepines can also be synthesized on a carboxy chip. Carboxy chips will also find application in the preparation of chips having synthesis initiation sites which are amines. In this aspect, the carboxy chips will be reacted with a suitably protected alkylenediamine to generate an amino surface.

Carboxy chips can be prepared by a variety of methods. In one group of embodiments, a solid support is derivatized with an aminoalkylsilane to provide a surface of attached amino groups. The derivatized surface is then treated with an anhydride such as glutaric anhydride to acylate the amino group and provide a surface of carboxylic acid functionalities. In other embodiments, the aminoalkylsilane is first reacted with an anhydride (i.e., glutaric anhydride) to generate a carboxylic acid silane which can then be coupled to the solid support, and similarly provide a surface of carboxylic acid residues.

V. Polymer-Coated Surfaces

The present invention also provides a method of preparing surfaces in which a polymer, having synthesis properties similar to a commercial peptide resin is attached to a solid support. The polymer films provide a porous three-dimensional matrix functionalized with reactive groups that serve as starting points for oligonucleotide or peptide synthesis. One of the potential advantages of these films in VLSIPS™ applications is that they may provide a much larger number of synthesis sites per unit area of substrate than is offered by the current generation of monofunctional silane-derivatized glass surfaces, while maintaining a similar or greater spacing between sites. Additionally, the use of an organic polymer on a solid surface will provide greater solvent compatibility and flexibility of the reaction site for attachment of the synthesis building blocks. Another advantage is the potential improvement in surfaces for performing bioassays which results from the variety of polymers available and the degrees of polymer porosity which can be obtained. The extent of binding of target molecules (receptors) to the immobilized oligonucleotide or peptide sequences (ligands) may be substantially increased, which enhances detection, and the multiplicity of binding sites within the polymer support may provide additional kinetic enhancement. Thus surfaces can be designed and prepared for optimum properties in a particular assay. This optimization will take advantage of the relatively thick but loosely woven polymer network that allows macromolecules to diffuse in and out of a layer of tethered ligands. Still other potential advantages that may be achieved with polymer-coated surfaces prepared by the present methods involve improved processing for reusing the surface, easier characterization of the surface for quality control in synthesis, and reduction of potential problems associated with the use of glass surfaces.

A variety of approaches can be employed for the preparation of polymer-coated solid surfaces. In one approach, the solid surface used is a rigid polymer which is then crosslinked with a "soft" polymer layer to confer desired surface properties. Alternatively, a solid surface such as a glass slide can be coated with a polymer film to form a composite. These composites can be created by covalently crosslinking the polymer to silanized glass, by in situ polymerization of monomers on a silanized glass surface, or by relying on the mechanical strength of a polymer film to completely wrap and adhere to a slide that has been dipped.

In any of these methods, the choice of available surface polymers is extensive. Suitable polymers include chloromethylated styrene-divinylbenzene (Merrifield resin), phenylacetamidomethylated styrene-divinylbenzene (PAM resin), and crosslinked polyethylene glycol-polystyrene grafts (TentaGel resin). Other polymers can be prepared as described below.

Selection of an appropriate surface polymer will include consideration of its compatibility with VLSIPS™ photochemistry conditions, flow channel synthesis conditions, or conditions used in alternative syntheses such as spotting techniques. For all of these techniques, the polymer must carry functional groups which are appropriate for the initiation of peptide, oligonucleotide or other small molecule synthesis. As a result, the polymer must be stable in the presence of the solvents and activating reagents used. When the polymer-coated surfaces are used in VLSIPS™ photochemistry, the UV transmittance of the polymer should be high and the optical quality should be uniform across the plane of the surface. For other applications, the compatibility of the surface polymer with VLSIPS™ bioassays will be of paramount importance, and the surface should exhibit low background fluorescence and Raman scattering. Additionally, the surface should exhibit low non-specific binding of receptors.

The polymers which are used to coat the solid support can also be selected based upon their functional groups which will serve as synthesis initiation sites. Typically, polymers having primary amine, carboxyl or hydroxyl functional groups will be selected.

Polymers having primary amine functional groups are of interest as these polymers can be readily adapted to coupling chemistry currently used in the VLSIPS™ process. Suitable polymers having primary amine functional groups include polyethyleneimine (linear or branched polymers, see Royer, G., *Chemtech*, pp. 694–700 (November 1974); Narayanan, S., et al., *Anal. Biochem.* 188:279–284 (1990); Rainsden, H., U.S. Pat. No. 4,540,486 (1995); Watanabe, K., et al., *Anal. Biochem.* 127:155–158 (1982); Meyers, W. et al., *J. Amer. Chem. Soc.* 99:6141–6142 (1977); Royer, G., et al., *J. Macromolec. Sci. Chem.* A10:289–307 (1976); Chao, K. et al., *Biotechnology and Bioengineering* 28:1289–1293 (1986)); polyacrylamide (see Inman, J., et al. *Biochemistry* 8:4074 (1967)); and polyallylamine which are all commercially available (Aldrich Chemical Company, St. Louis, Mo., USA; Polyscience, location; and Dow Chemical Company, Midland, Mich., USA). Other polymers, such as polydimethylacrylamide, can be synthesized according to published procedures (see Atherton, E., et al. in *Solid Phase Peptide Synthesis: A Practical Approach*, Chapter 4, pp. 39–45, IRL Press (1989); and Arshady, R., et al., *J. Chem. Soc. Perkin. Trans.* 1:529 (1981)). Structures for these polymers are provided in FIG. 3. Additionally, these polymers are soluble in polar solvents such as water, methanol and DMF.

Polymers having carboxyl functional groups are also useful as the resulting surfaces are very hydrophilic. Furthermore, the synthesis initiation sites (i.e. the carboxylic acid groups) are useful in peptide synthesis which proceeds from the amino terminus of the peptide to the carboxylic acid terminus. Suitable polymers having carboxylic acid functional groups include poly(acrylic acid), poly(ethylene/maleic anhydride), and poly(methylvinyl ether/maleic anhydride) shown in FIG. 4.

Polymers having hydroxyl functional groups are also useful as the resulting surfaces are extremely wettable. Examples of suitable polymers include polyethyleneglycol (PEG, see Rapp Polymere Catalogue, Harris, J., *J. Polym. Sci. Polym. Chem. Ed.* 22:341 (1984); and Pillai, V., et al., *J. Org. Chem.* 45:5364–5370 (1980)); poly(vinyl alcohol); and carbohydrates (see *J. Chemical Society Chem. Comm.*, p. 1526 (1990)) which are shown in FIG. 5. Solid supports coated with carbohydrate polymers or glycans are discussed in Section VI, below.

Figure 6:
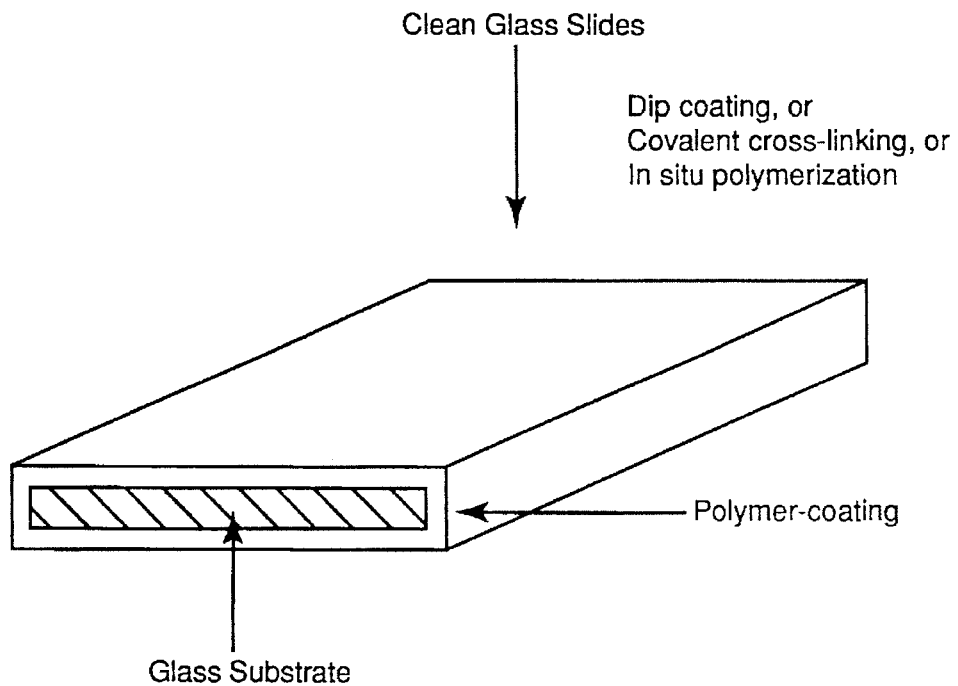
FIG. 6 is an illustration of a polymer-coated glass substrate which can be prepared by dip coating, covalent crosslinking or in situ polymerization.

The preparation of thin polymers films on solid surfaces can be accomplished using a variety of methods including dip coating, covalent attachment and in situ polymerization (see FIG. 6).

Dip Coating

Figure 7:
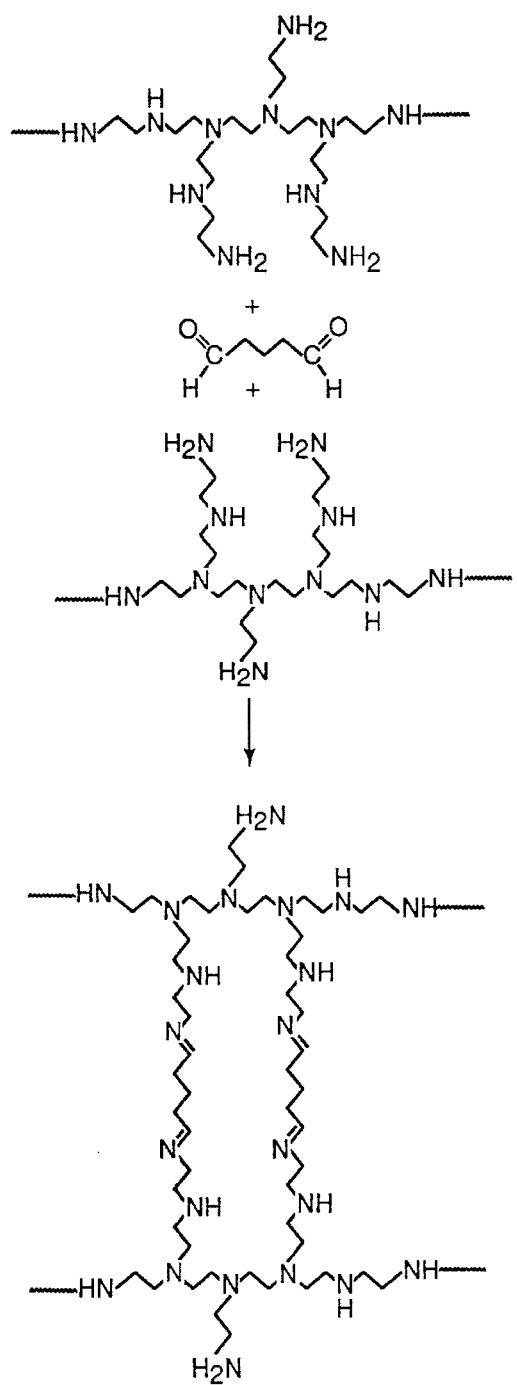
FIG. 7 illustrates one example of polymer crosslinking which uses glutaraldehyde and polyethyleneimine.

Films can be created on solid substrates by dip coating with the polymer solution, followed by evaporation of the solvent and stabilization of the coating using crosslinking agents or UV treatment. Suitable crosslinking agents will depend on the nature of the functional groups present in the polymer. For polymers having primary amine functional groups, crosslinking agents such as glutaraldehyde or Xama (a polyfunctional aziridine: see, Watanabe, et al., *Anal. Biochem.* 127:155–158 (1982)) are preferred. Crosslinking agents which are useful for other polymers are known to those of skill in the art. Additionally, the degree of polymer crosslinking can be varied to produce films which are optically transparent and of uniform thickness. A related method of producing a uniform thickness polymer coating utilizes a spin-coating technique. FIG. 7 illustrates a typical reaction scheme for the preparation of polyethyleneimine-coated glass substrates.

Covalent Attachment

Figure 8:
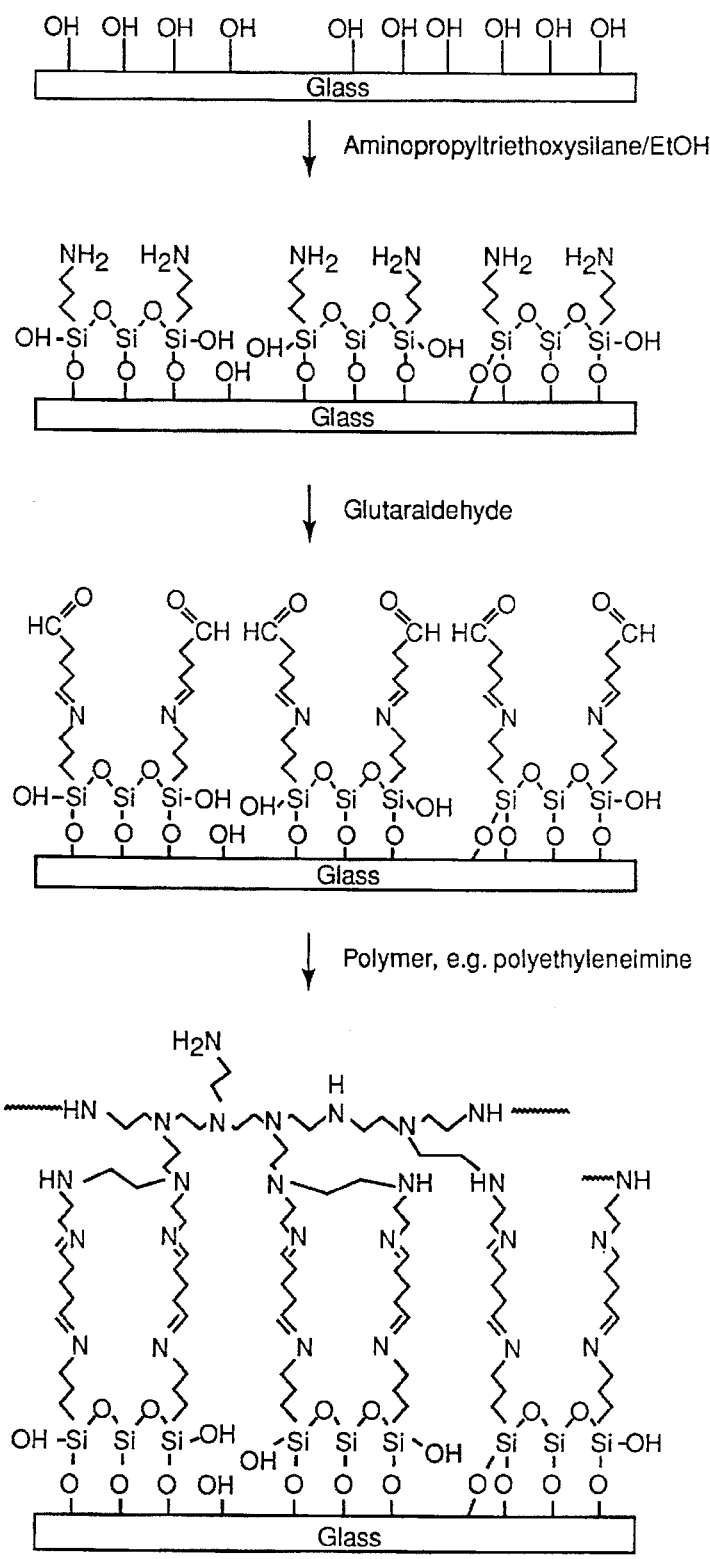
FIGS. 8–11 illustrate a variety of methods for covalently attaching a polymer to a derivatized solid support.
Figure 9A:
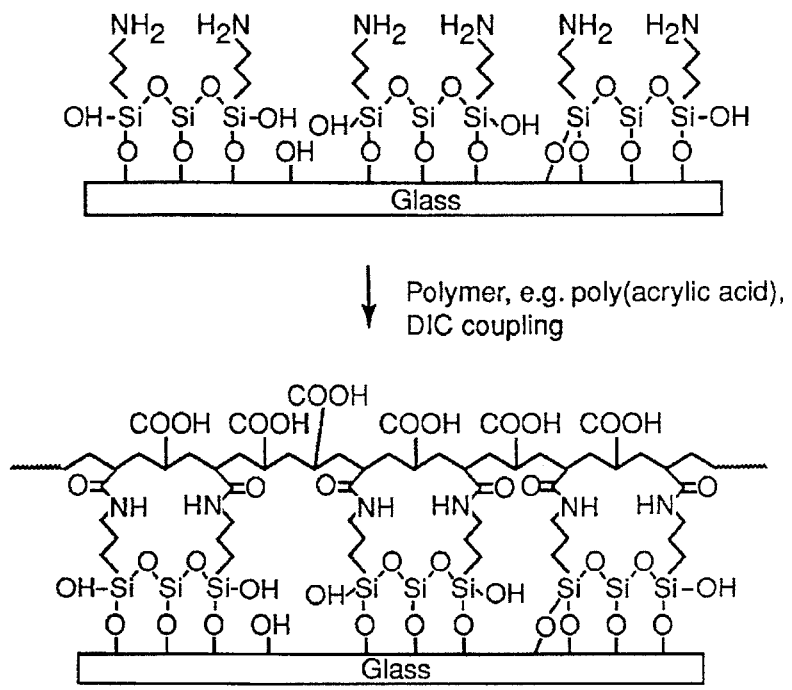
Figure 9B:
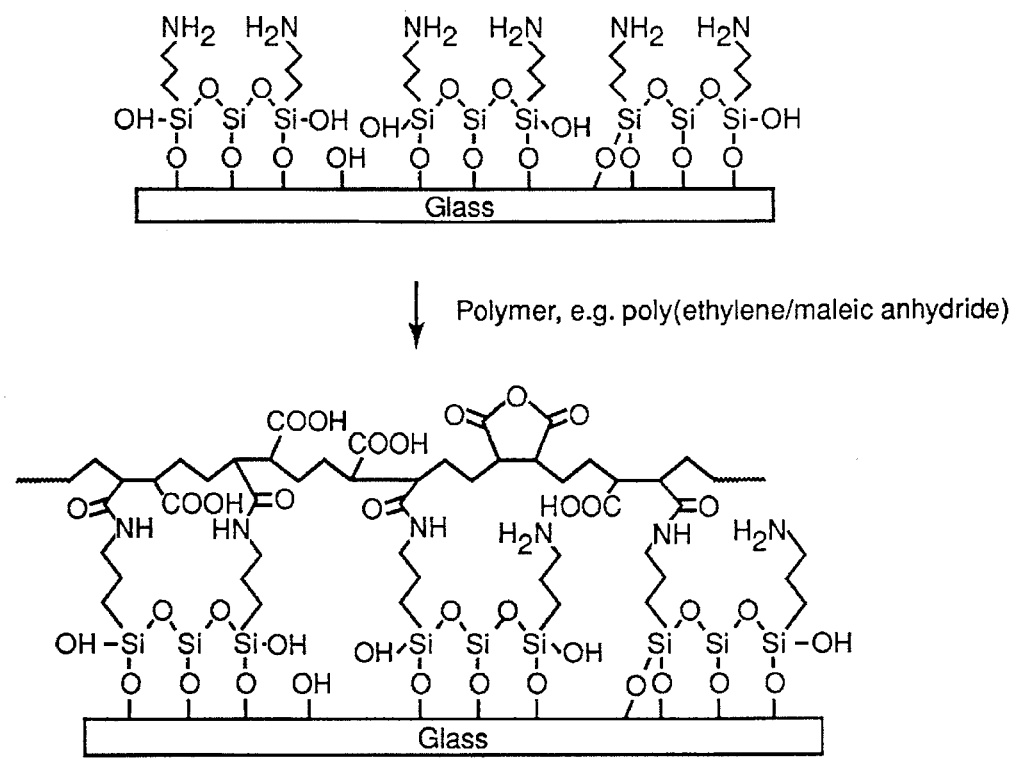
Figure 10:
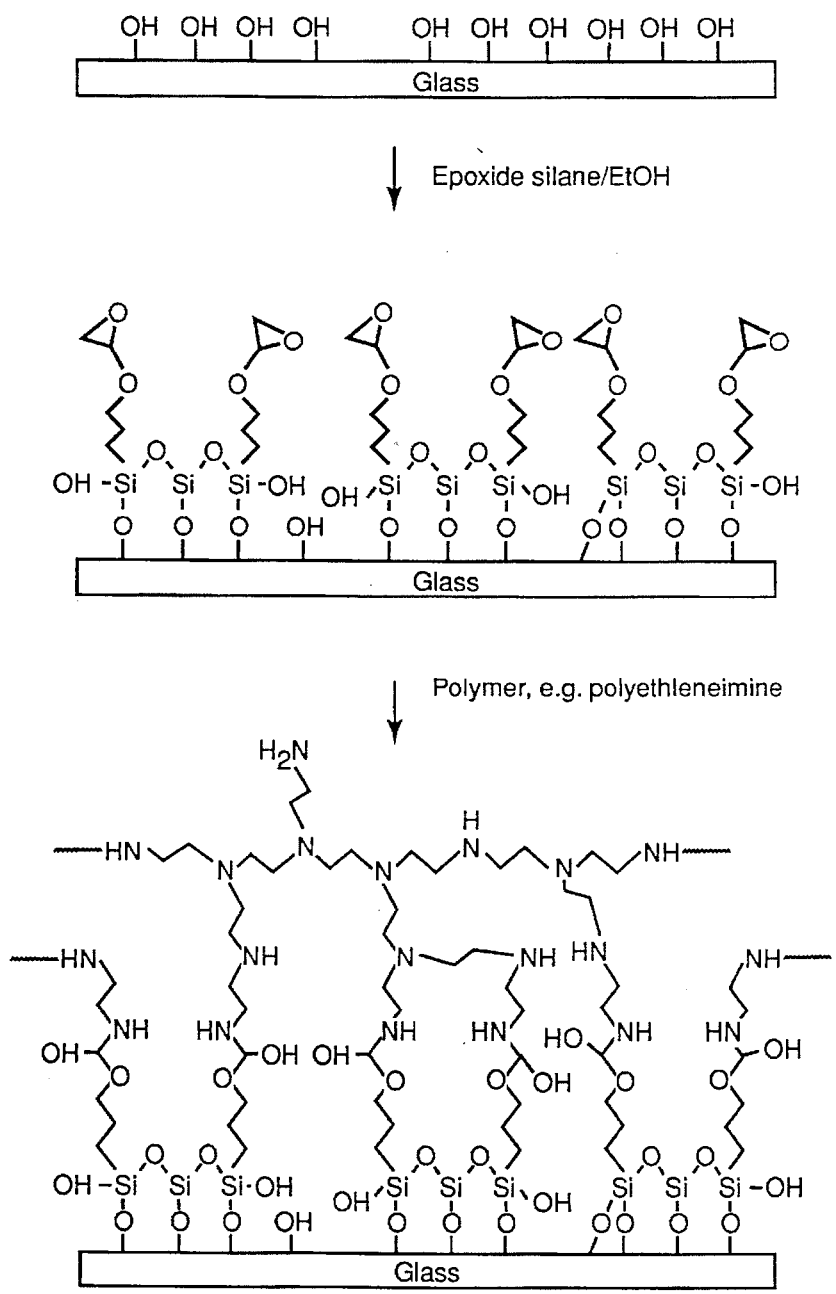
Figure 11:
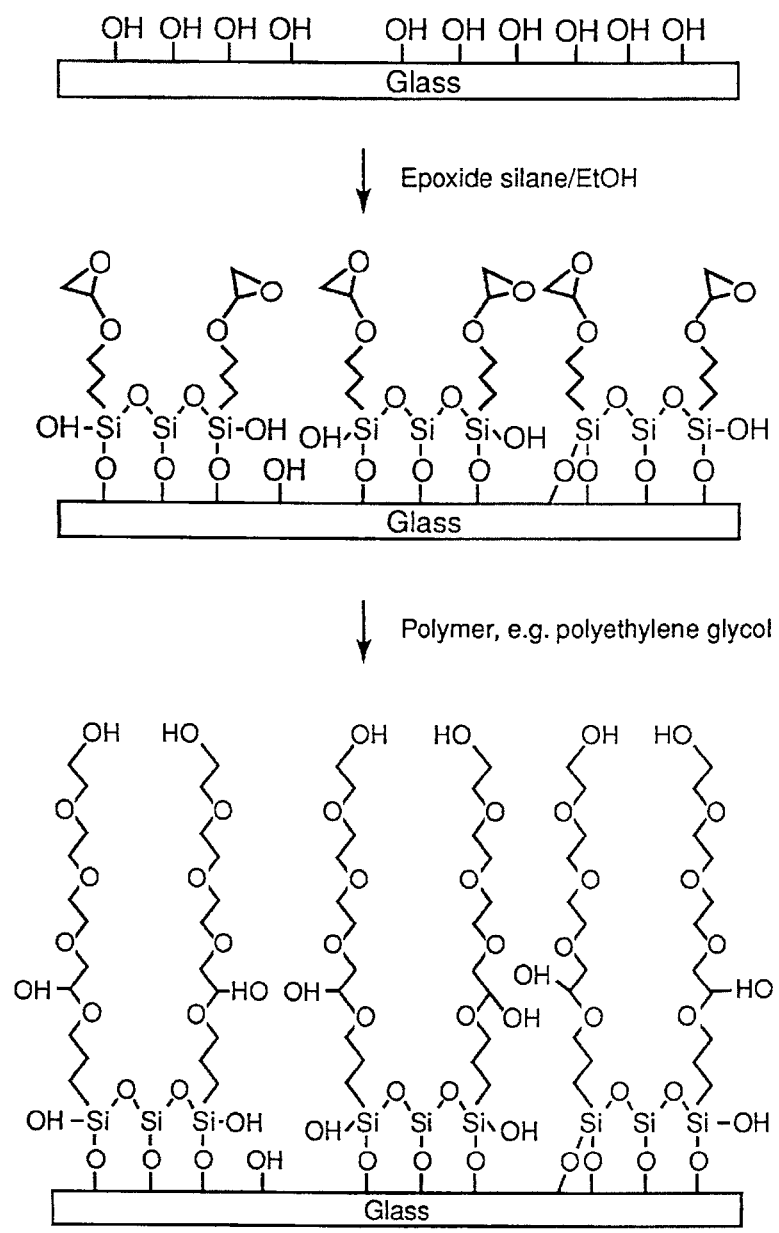

Another method for the preparation of polymer films on solid surfaces involves preparation of the selected polymer followed by covalent attachment of the polymer to functional groups which are present on the substrate surface or modified substrate surface. In one embodiment, a glass surface is cleaned and silanized using an aminopropyltriethoxysilane to provide a glass surface having primary amine functional groups. The amine functional groups can then be reacted with crosslinking groups (such as glutaraldehyde) and treated with solutions of an appropriate polymer (see FIG. 8). Alternatively, glass surfaces which have been modified with aminopropylsilanes can be reacted with polymers having carboxylic acid functional groups (using, for example, water soluble carbodiimides) or by direct reaction of the modified surface with a polymer having attached anhydride groups (see FIG. 9). In other embodiments, glass surfaces can be silanized with silanes having epoxide functional groups and subsequently reacted directly with polymers having either amine or hydroxy functional groups (see FIGS. 10 and 11). In addition, glass surfaces can be planarized by using polysiloxanes known as "spin on glasses" which may provide both a more uniform planar surface and/or a substantially higher density of functional sites which further provides for better subsequent derivatization.

In Situ Polymerization

Figure 12:
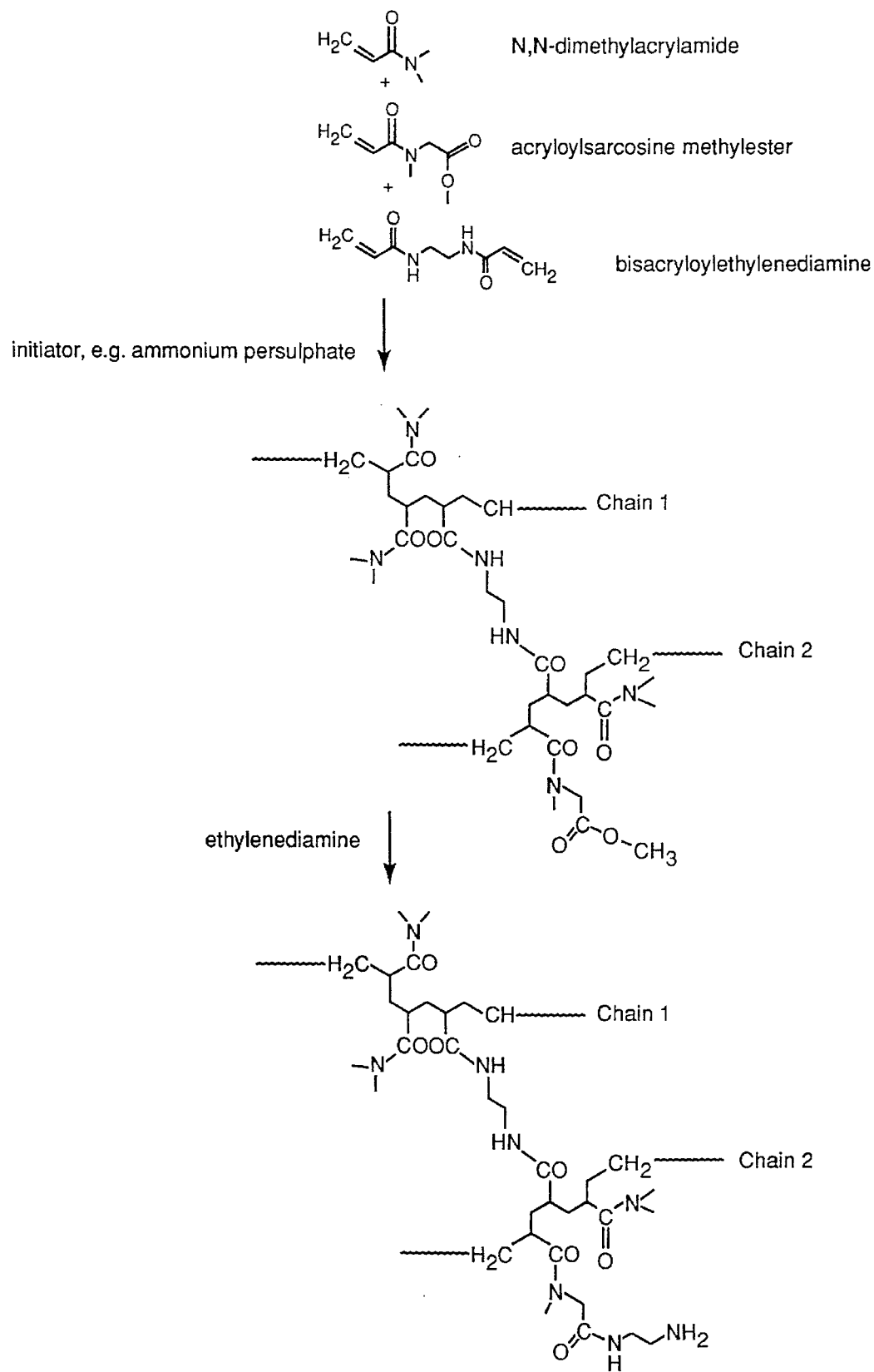
FIG. 12 illustrates in situ polymerization which can be used to prepare a polymer-coated solid support.

For polymers that are not commercially available, polymer-coated substrates can be formed by carrying out the polymerization reaction on the substrate surface. For example, a mixture of appropriate monomers are dissolved in solvent with an initiator. After a suitable activation period, the solid substrate is dipped into the mixture and then cured at elevated temperatures to complete the polymerization. The resulting surfaces are then washed, dried and functionalized to provide functional groups which are useful as synthesis initiation sites (see FIG. 12).

Still other methods of preparing polymer-coated solid supports will use combinations of two or more of the above methods. For example, a polymer film can be "grafted" onto a glass support by first silanizing the glass with an acrylamido-alkyl trialkoxysilane. Subsequent polymerization of an acrylamide copolymer layer on top of the silanized glass provides a covalently attached film which exhibits excellent resistance to all of the conditions used for oligonucleotide synthesis, deprotection and hybridization.

The polymer-coated support can be tailored to provide optimal properties for synthesis and for biological assays. For example, the final concentration of functional groups (amine or hydroxyl) in the polymer can be controlled by varying the relative amounts of nonfunctionalized and functionalized monomers used in forming the polymer. Additionally, the porosity and solubility of the polymer films can be controlled by varying the concentrations of monomers and crosslinking agents in the composition. Thus, a high degree of crosslinking gives a rigid insoluble polymer with low pore size, whereas omitting the crosslinking agent altogether will result in soluble linear polymer chains (with functional groups) extending off the surface of the substrate from the attachment sites.

Prior to use in synthesis, polymer-coated surfaces can be examined for the existence and uniformity of the polymer film using visual inspection, contact angle (wettability) measurements, fluorescence labeling or infrared spectroscopy.

The resulting polymer-coated surfaces in which the polymer layer is uniform in thickness and optically transparent and which exhibit low background fluorescence can be attached to a linker molecules for subsequent use in synthesis. Suitable linker molecules include 15-ATOM-PEG, and other linkers described in co-pending U.S. application Ser. No. 08/374,492, filed Jan. 17, 1995 and incorporated herein by reference.

One of skill in the art will understand that the present invention is not limited to planar glass surfaces, but is equally useful when applied to other surfaces, for example, glass beads.

VI. Glycan-Coated Surfaces

In still another aspect, the present invention provides solid surfaces which are coated with a layer of high molecular weight (500 Kd) dextran ($\alpha$1-6 poly D-glucose). Solid surfaces which are coated with dextran or other glycans provide more hydrophilic surfaces which exhibit improved characteristics for monitoring the binding of a receptor to a support-bound ligand.

In general, the glycan-coated surfaces can be prepared in a manner analogous to the preparation of polymer-coated surfaces using covalent attachment. Thus, a glass surface can be modified (silanized) with reagents such as aminopropyltriethoxysilane to provide a glass surface having attached functional groups (in this case, aminopropyl groups). The modified surface is then treated with a solution of a modified dextran to provide a surface having a layer of dextran which is covalently attached.

The method of covalently attaching a dextran or other carbohydrate to the glass surface can be carried out using a variety of chemical manipulations which are well known to those of skill in the art. In one embodiment, the surface is modified to produce a glass surface having attached primary amine groups using reagents such as aminopropyltriethoxysilane. The resulting amines are then reacted (using water soluble carbodiimides) with dextrans which have been previously modified with carboxymethyl groups. In another embodiment, the glass surface is modified with hydroxy groups using reagents such as hydroxypropyltriethoxysilane. Subsequent reaction of the hydroxy moiety with epichlorohydrin provides a surface having attached epoxide functional groups. The epoxides can then be reacted directly with hydroxyl groups present in dextran to provide covalent attachment of the dextran to the modified surface.

Following covalent attachment of the dextran to the glass surface, the carbohydrate can be further derivatized to provide synthesis initiation sites for peptide, oligonucleotide or other small molecule synthesis. For example, treatment of dextran-modified surfaces with bromoacetic acid results in derivatives having attached carboxymethyl groups. The carboxylic acid groups can be used as synthesis initiation sites or they can be further modified with lower diaminoalkanes to provide primary amines as synthesis initiation sites. See, Cass, et al., In PEPTIDES: CHEMISTRY, STRUCTURE AND BIOLOGY, Hodges, et al., eds., ESCOM, Leiden pp. 975-977 (1994).

VII. Reusable Chips

A number of methods of forming ligand arrays have been discussed in the above General Methods section and in the Background of the Invention. Typically, the ligand arrays are prepared and used for a single binding experiment, either as a method of diagnosis (detecting the presence of a particular receptor of interest) or to determine the binding affinity of a number of different ligands for a receptor. Following the experiment or diagnosis, the ligand array is often discarded.

The present invention also provides a method of regenerating the surface of used ligand arrays or arrays upon which a binding experiment has already been conducted. The surfaces are regenerated in a manner which allows a subsequent binding experiment to be carried out. Using this method, ligand arrays which are used, for example, for diagnostic purposes can be regenerated and reused in multiple applications, thereby reducing the costs associated with diagnosis.

In one group of embodiments, used ligand arrays are treated with a solution of a chaotropic reagent to remove any bound receptors. The resulting arrays can be used directly in another assay or the array can be placed in a storage solution which retards degradation of the ligand array. The chaotropic agents which are useful in the present method are selected depending upon the receptor which is to be removed from the surface. In preferred embodiments, the chaotropic reagent is a member selected from the group consisting of guanidine hydrochloride, urea, glycine, Tris and guanidine with dithiothreitol. For ligand arrays of peptides to which a protein is bound, the preferred chaotropic agents are guanidine hydrochloride, urea, or glycine hydrochloride pH 2.0. For removal of tightly bound receptors such as antibodies, a mixture of guanidine and dithiothreitol is preferred. For removal of DNA which is bound to another oligonucleotide ligand, the preferred chaotropic reagent is 10 mM Tris, 0.1 mM EDTA.

In another group of embodiments, the cleaned and regenerated ligand array is placed into a storage solution.

The present inventive method can be applied to a wide variety of solid supported ligand arrays including those which are formed according to any of the methods described in the above General Methods section. Additionally, the present method of surface regeneration can be used for any of the ligand arrays formed on the polymer-coated solid supports, also discussed above. In preferred embodiments, the used ligand array is a VLSIPS™ chip.

In other embodiments, a second or competing ligand is included with the chaotropic reagent to further inhibit rebinding of the receptor to the surface.

VIII. Methods for Oligomer Synthesis

Figure 16:
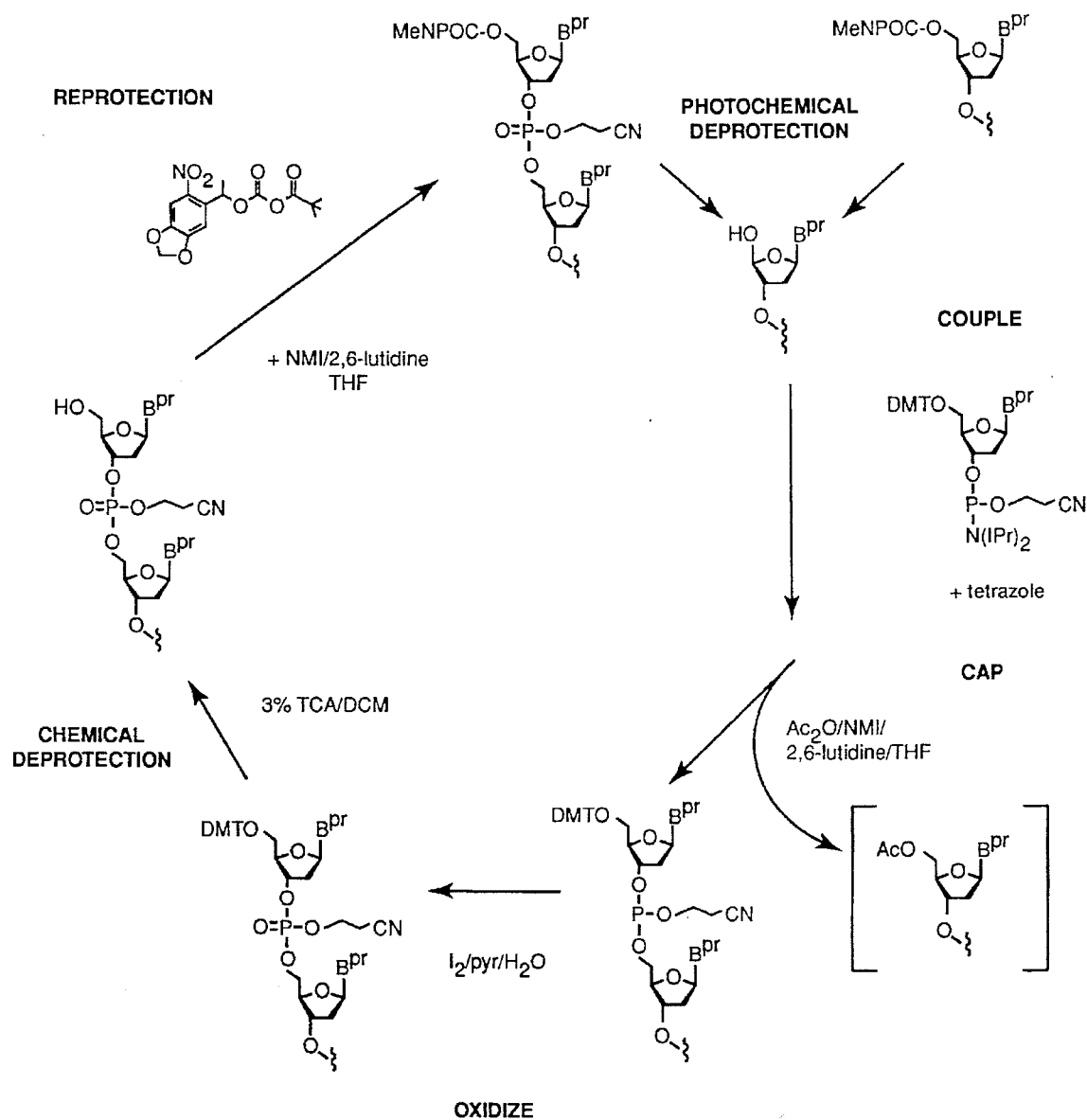
FIG. 16 illustrates a method for the synthesis of oligonucleotides in which the protecting groups are cleaved and replaced as part of the synthesis cycle.
Figure 17:
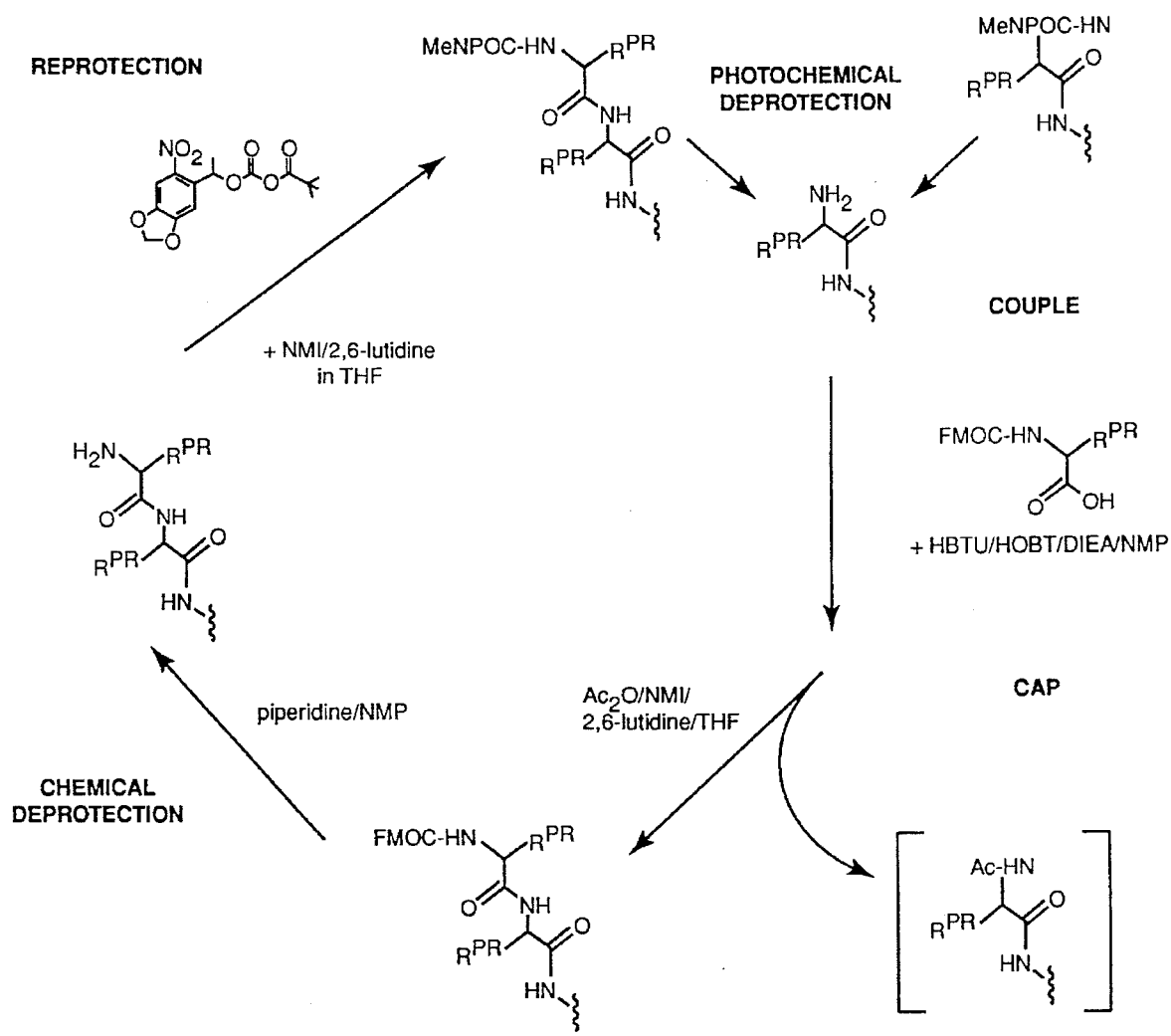
FIG. 17 illustrates a method for the synthesis of peptides in which the protecting groups are cleaved and replaced as part of the synthesis cycle.

The present invention also provides methods for the synthesis of oligomers on a solid support. General methods for the synthesis of oligomers on solid supports have been described above. Thus, the present invention provides methods for the synthesis of oligomers on a solid support wherein the protecting groups on the monomers used in the oligomer preparation are exchanged following addition of the monomer to the growing oligomer. This is illustrated in FIGS. 16 and 17 for the preparation of oligonucleotides and peptides, respectively. As shown in FIG. 16, a solid support having preselected regions is first constructed which has attached photolabile protecting groups in each of the preselected regions. Using photolithographic techniques described in the above-noted General Methods section, the photolabile protecting groups can be removed in one preselected area and a monomer bearing a chemically-removable protecting group is attached. Standard, chemically-removable protecting groups include those groups which are commercially available and which are known to be removable under typical chemical conditions. Examples of such protecting groups include FMOC, DMT, BOC, t-butyl esters and t-butyl ethers. Following the attachment of such a protected monomer, the protecting group is removed under conditions described in, for example, Greene, et al., *Protective Groups In Organic Chemistry*, 2nd Ed., John Wiley & Sons, New York, N.Y., 1991, previously incorporated herein by reference. The reactive functionality which was previously protected with the chemically-removable protecting group is then re-protected with a photolabile protecting group, using, for example, a derivative of the formula:

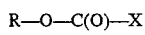

in which R is a photo-cleavable moiety (e.g., o-nitrobenzyls, pyrenylmethyl, Ddz, various benzoin groups, bromonitroindole) and X is a suitable leaving group (e.g., Cl, F, pentafluorophenoxy, p-nitrophenoxy, N-succinimidyloxy, adamantanecarboxy, or tetrazolyl). Preferably the derivative is a suitably activated derivative of the MeNPOC or NVOC groups. Examples of suitably activated derivatives include such reagents as mixed anhydride derivatives of MeNPOC (e.g., MeNPOC-pivaloate prepared from the reaction of MeNPOC chloride with triethylammonium pivaloate) or carbonates of MeNPOC (e.g., the carbonate produced by the reaction of MeNPOC chloride with pentafluorophenol). The re-protection of surface functional groups with such reagents is typically carried out in an organic solvent containing a non-nucleophilic base (e.g., 2,6-lutidine, pyridine, triethylamine or diisopropylethylamine). In some embodiments, a nucleophilic catalyst (e.g., N-methylimidazole, hydroxybenzotriazole or 4-(N,N-dimethylamino)pyridine) is also included to provide further enhancement of the rate and efficiency of the re-protection step. Following the addition of the photolabile protecting groups, the VLSIPS cycles can be continued using photolithographic deprotection, followed by coupling of an additional monomer, protecting group replacement, etc., until the desired oligomer are completed. Preferably, the cycle is repeated from 1 to 120 times.

In one group of embodiments, the oligomer produced is an oligonucleotide. As noted above, FIG. 16 illustrates the method for oligonucleotide synthesis. While this Figure illustrates the use of phosphoramidite chemistry for monomer coupling, monomers can also be added to the growing oligomer using H-phosphonate methods or other coupling methods known to those of skill in the art. Additionally, the photolabile protecting group which is illustrated (MeNPOC) can be replaced with another photolabile protecting group such as NVOC, or those photolabile protecting groups described in co-pending Application PCT/US93/10162 (filed Oct. 22, 1993) and previously incorporated herein by reference. Once the chemically-removable protecting group has been removed, a photolabile protecting group can be added using a mixed anhydride of the protecting group.

In another group of embodiments, the oligomer is a peptide (see FIG. 17). For peptide synthesis, commercially-available amino acids having chemically-removable protecting groups are used, for example FMOC-amino acids. After exchange of the protecting groups, the coupling steps can be carried out using BOP/HOBt activation and coupling methods. Those of skill in the art will understand that other coupling methods as well as other amino acid monomers having chemically-removable protecting groups can be used in the present invention.

In still another group of embodiments, all preselected areas are derivatized with a first monomer, each of the monomers having a chemically-removable protecting group. Following the addition of the first monomer to each of the preselected regions, the protecting groups are all removed in a single step using chemical deprotection in the form of a wash across the solid support. Reprotection of each of the growing oligomers with a photolabile protecting group is then carried out in the form of another wash across the entire solid support. Following this reprotection, photolithographic techniques of oligomer synthesis can be continued using monomers having chemically-removable protecting groups.

The present method provides certain advantages over conventional VLSIPS synthesis. For example, a number of monomers having chemically-removable protecting groups are commercially available.

IX. Examples

The following examples are offered solely for the purposes of illustration, and are intended neither to limit nor to define the invention.

EXAMPLE 1

This example illustrates the "standard process" of surface derivatization and the "doped process" of surface derivatization.

Standard Process of Surface Derivatization

Figure 2:
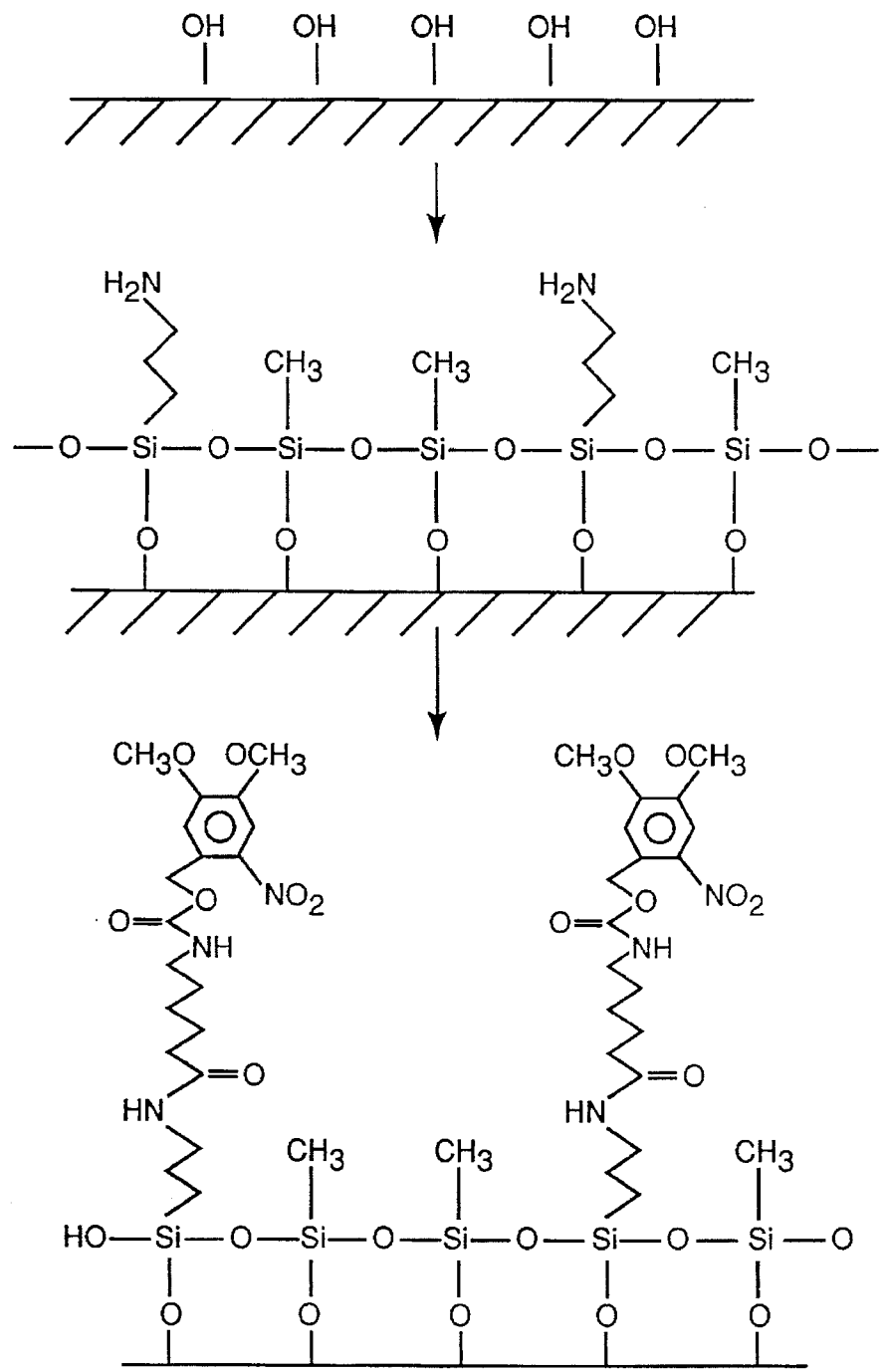
FIG. 2 illustrates a standard process of substrate derivatization.

The standard process of surface derivatization is described below with reference to the illustration presented in FIG. 2. Glass microscope slides are cleaned by treatment with a Nochromix/sulfuric acid cleaning solution. The slides are then etched with 10% NaOH for three minutes at 70° C., rinsed with 1% HCl, and finally rinsed with ethanol to provide a substrate having exposed hydroxyl groups. The resulting clean glass substrates are then treated with a 1% silane solution (1:10 mole ratio of 3-aminopropyltriethoxysilane:methyltriethoxysilane) in dichloromethane for 15 minutes. After standing at room temperature for 30 minutes the substrates are then cured at 100° C. for 15 minutes to provide aminopropyl silylated substrates. The amino groups which are present are then acylated with NVOC-aminocaproic acid, using standard BOP coupling techniques. After 2 hours, any unreacted amino groups are capped as their acetamides using acetic anhydride to provide a derivatized surface having attached NVOC-aminocaproic acid spacing groups.

Doped Process of Surface Derivatization

The doped process of surface derivatization is described below with reference to the illustration presented in FIG. 1. A glass microscope slide is cleaned as described above in the standard process. The resulting clean glass substrate is treated with a 1% silane solution (aminopropyltriethoxysilane in dichloromethane) for 15 minutes. After standing at room temperature for 30 minutes, the substrate is cured at 100° C. for 15 minutes. To the aminopropyl silylated substrate is added a diluent mixture of NVOC-aminocaproic acid and a suitably protected amino acid (presented as "R" in FIG. 1). The species in the mixture are coupled to the amino group now present on the substrate using BOP chemistry. After 2 hours, any remaining amino groups present on the substrate are capped using acetic anhydride to provide a surface having a predetermined density of linking groups per unit area.

EXAMPLE 2

This example illustrates the characterization of a substrate prepared according to the "doped process" in Example 1.

Surface Density of Functional Groups

The density of NVOC-protected amine on a derivatized surface was assessed using the NVOC photoproduct fluorescence assay. Substrates were prepared according to the doped process in Example 1 using either acetylated glycine or serine to dilute the number of NVOC-aminocaproic acid linking groups being coupled to a glass surface having attached aminopropylsilanes. The surfaces were labeled with a 39:1 mixture of phenylisothiocyanate to fluorescein isothiocyanate in the labeling solution (10 mM total isothiocyanate in 1% DIEA/NMP was used in order to minimize fluorescence quenching effects). For photolysis, a solvent of 5 mM $H_2SO_4$ in dioxane was used with illumination at 365 nm and at about 10 mW/cm$^2$ for up to 12 minutes. After photolysis of the NVOC-protected surfaces and collection of the solvent used, fluorescence emission was measured at 400 nm in a spectrofluorimeter following a 330 nm excitation.

Figure 13:
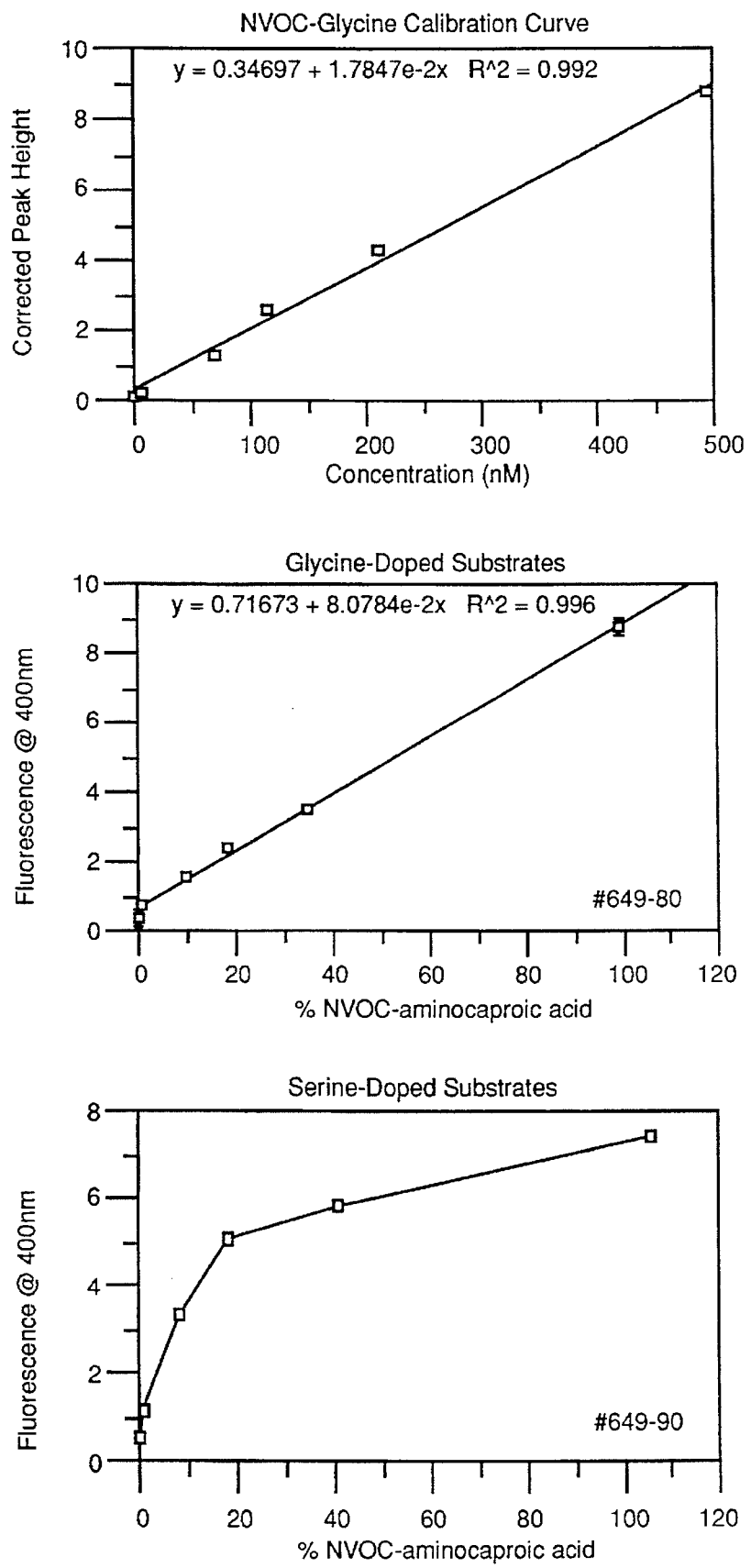
FIG. 13 provides a comparison of glycine-doped and serine-doped surface derivatization.

The results are presented in FIG. 13. The linear relationship observed for the glycine-doped series implies that the rates of coupling for the two components with the surface are similar. The nonlinear but reproducible relationship observed for the serine-doped surfaces, although not fully understood, implies either that the components react with the aminopropylsilane surface with different rates, or that some loss of the FMOC group occurs under the reaction conditions, resulting in enhanced coupling of the NVOC-protected linker at the higher serine-to-linker ratios. However, the reproducibility of the curve implies that the approach may still be used to control site density. Comparison of the fluorescence signals to a calibration curve generated from known concentrations of NVOC-glycine in solution allows for an estimate of site spacing on a surface to be made. Table 1 summarizes these results.

TABLE 1

Site Density on Substrate Surfaces

| % NVOC | Site Density # sites per $\mu m^2$ | Average Spacing Angstroms |
|---|---|---|
| Glycine-Doped Substrates | | |
| 100 | 338,000 | 17.2 ± 0.5 |
| 33 | 118,000 | 29.1 |
| 17 | 74,000 | 36.8 |
| 9 | 41,000 | 49.4 ± 1.4 |
| 1 | 6,800 | 121.2 ± 30.7 |
| Serine-Doped Substrates | | |
| 100 | 299,000 | 18.3 |
| 33 | 220,000 | 21.3 |
| 17 | 192,000 | 22.8 |
| 9 | 121,000 | 28.8 |
| 1 | 24,000 | 64.3 |

Chemical Coupling Efficacy of Doped Substrates

Yields for manual coupling of single amino acid residues onto the derivatized substrate surfaces were estimated using the fluorescence labeling protocol described above in Example 2. Results for coupling of NVOC-glycine and NVOC-serine are presented in Table 2. As the data indicate, an improvement in coupling efficiency is observed as site density decreases.

TABLE 2

Estimated Yields of Coupling Reactions

| % NVOC | NVOC-Glycine | NVOC-Isoleucine |
|---|---|---|
| Standard Substrates | | |
| 100 | 81.1 ± 6.2 | 81.8 ± 5.6 |
| Glycine-Doped Substrates | | |
| 100 | 85.8 ± 2.7 | 89.2 ± 8.0 |
| 10 | 97.3 ± 14.9 | 99.8 ± 10.5 |
| 1 | 101.4 ± 0.8 | 101.1 ± 4.3 |

Wettability—Contact Angle

Substrate surfaces were characterized with respect to solvent wettability using the technique of contact angle measurement as described in American Standard Test Method C813-90, and Bush, et al., *Amer. J. Optometry Physiol. Optics* 65:722–728 (1988), incorporated herein by reference. Contact angle (the angle between the tangent to the liquid/vapor interface of a solvent droplet and the surface upon which it rests) is a measure of the "wettability" of the surface. Non-zero angles imply that the liquid is nonspreading on that surface. Thus, for water, small angles indicate a hydrophilic surface and large angles indicate a hydrophobic surface. The results for contact angles measured on standard and doped surfaces is presented in Table 3. All surfaces were wettable by the organic solvents used in peptide coupling procedures. Surfaces doped with the serine moiety were significantly more hydrophilic than those prepared using the standard process.

TABLE 3

Contact Angle for Doped Substrates

| Solvent | Surface | Contact Angle |
|---|---|---|
| Deionized Water | Standard | 55.7 ± 1.9 |
| Deionized Water | Standard (deprotected) | 57.5 ± 1.0 |
| Deionized Water | 100% NVOC | 51.3 ± 1.5 |
| Deionized Water | 10% NVOC Glycine-Doped | 43.0 ± 1.9 |
| Deionized Water | 10% NVOC Serine-Doped* | 31.3 ± 1.6 |

*side-chain hydroxyl deprotected

EXAMPLE 3

This example illustrates the differences in contact angle and surface wettability which can are achieved using various linking groups.

Contact angle measurements of a surface with various solvents is an established means of characterizing the wettability or hydrophilicity of a surface. We have used the sessile drop method (American Standard Test Method C813-90) with deionized water as a technique to measure the hydrophilicity of various surfaces employing a laser-assisted device described by Bush (Bush et. al., *Amer. J. Optometry Physiol. Optics* 65:722–728 (1988)). In general, the lower the contact angle, the more wettable or water-like (hydrophilic) is the surface. Control experiments with known surfaces such as Teflon, nylon, and polystyrene demonstrated that we could reproduce the literature values for these types of surfaces and allowed us to calibrate our device.

Figure 14:
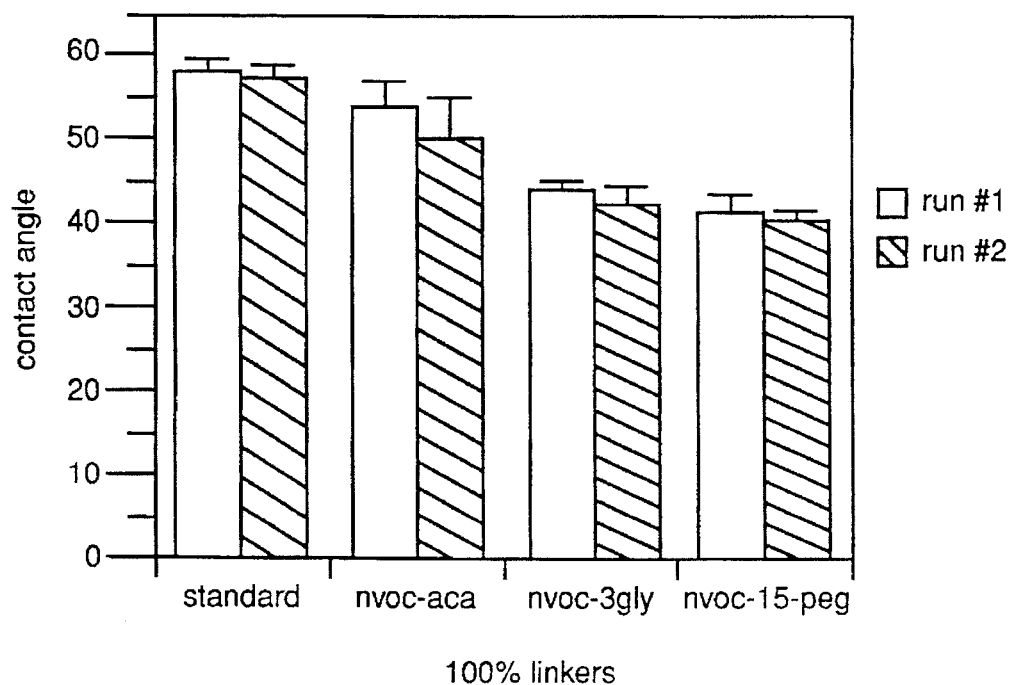
FIG. 14 is a graph showing contact angle data for substrates having various linking groups.

Several aminopropylsilane slides were prepared via two different techniques. In general, the two techniques for surface derivatization differed in the amount of aminopropylsilane used to initially coat the surface: in the "standard process" the surface was derivatized with a 10:1 mixture of methyltriethoxysilane:aminopropyltriethoxysilane whereas in the "doped process" pure aminopropylsilane was used. The two types of surfaces were subsequently derivatized with three different NVOC-protected linkers (NVOC-CAP, NVOC-TRIGLY, or NVOC-15-ATOM-PEG) as previously described with BOP/HOBt activation. The respective contact angles with water were determined with the NVOC group still present and are illustrated in FIG. 14. The aminocaproic acid derived slide prepared via the "standard process" was found to have the largest contact angle and was hence the least hydrophilic, whereas the aminocaproic slide prepared via the "doped process" was found to be slightly more hydrophilic. Both the 15-ATOM-PEG and TRIGLY surfaces were found to possess the lowest contact angles and were thus the most hydrophilic. The contact angle measurements for the derivatized surfaces are thus in general agreement with results obtained in an HPLC assay.

EXAMPLE 4

This example illustrates the relative amounts of specific and non-specific binding which can be achieved between a substrate on a solid support and a receptor utilizing a variety of linking groups.

As a model for studying the interplay of site density, surface wettability, and linker length on binding of macromolecules to various surfaces, the binding of labeled strepavidin to biotinylated surfaces was examined. This system was chosen because of its extensive use for immunoassay development, the commercial availability of high quality fluorescently-labeled reagents, and the simplification of working with a ligand receptor pair with a high affinity for each other (determined to be $10^{-15}$M, see M. Green, *Adv. Protein Chem.*, 29:85–133 (1975)).

Several slides with differing surfaces were prepared as above and were then subjected to photolysis in order to remove the terminal NVOC group. Biotin was coupled onto the liberated amino group via BOP/HOBt activation of the acid functionality of the biotin molecule, to provide biotinylated surfaces in which the nature of the linker joining the biotin to the surface differed. Eight different surfaces were prepared: one labeled "standard aminocaproic" which is described above as "standard process" and seven other surfaces in which the ratio of linker to diluent was varied as described above as "doped process". The diluent molecule was either N-acetyl glycine or N-acetyl serine and the ratios tested were either 100% linker/0% diluent or 10% linker/90% diluent. A template was clamped onto the surface of each slide which segregated the surface into 3 individual wells. A Buna-N gasket was used to seal the template to the surface. Commercially available fluorescein-labeled strepavidin and strepavidin (Molecular Probes Inc., Eugene, Oreg., USA) were used as a mixture in order to minimize fluorescence self quenching effects. Surface-bound fluorescence was measured via confocal fluorescence microscopy employing the excitation and emission wavelengths of fluorescein. Control experiments (data not shown) demonstrated that using ratios of labeled strepavidin to strepavidin of 0.05–1:1 respectively, resulted in little or no fluorescence self quenching being observed. Control experiments (data not shown) also demonstrated that 2 hr incubation times were sufficient to achieve equilibrium between the surface-bound biotin and solution-strepavidin.

Following incubation of the surface with the mixture of labeled strepavidin/unlabeled strepavidin in PBS/Tween-20 buffer for 2 hr, the wells were washed with buffer and surface-bound fluorescence was measured. Non-specific binding of strepavidin to the surface was measured by preincubation the strepavidin mixture with excess biotin (in solution) to block the binding sites, followed by incubation of the blocked strepavidin with the surfaces as before. Non-specific binding was subtracted from the measurements determined above to give a net binding signal, which is illustrated in FIG. 15. Larger net binding signals are indicative of greater discrimination between specific and non-specific binding. As is observed from the graph, the surface prepared from 15-ATOM-PEG exhibited the greatest discrimination between specific and non-specific binding.

EXAMPLE 5

This example illustrates the surface derivatization of a glass slide with a carboxysilane to produce a carboxy "chip" which is subsequently derivatized with an FMOC protected 15-ATOM-PEG linking group.

(a) Preparation of N-triethoxysilylpropylglutaramide

To a solution of aminopropyltriethoxysilane (3.0 g, 13.55 mmol, Petrarch Systems, Bristol, Pa.) in 35 mL of $CH_2Cl_2$ was added glutaric anhydride (1.54 g, 13.50 mmol) at room temperature. The reaction mixture was warmed slightly upon addition of the anhydride. After stirring for 2 hours, the solvent was removed under reduced pressure to yield 4.5 g of a colorless oil. NMR analysis indicated that the product was 95% pure and no further purification was performed.

(b) Surface Derivatization

Glass microscope slides were derivatized as described previously under the "standard process". Thus a 1% solution of 1:10 N-(triethoxysilylpropyl)glutaramide:methyltriethoxysilane in $CH_2Cl_2$ was prepared and freshly cleaned microscope slides were immersed into the solution for 15 minutes. The slides were briefly rinsed with $CH_2Cl_2$ and allowed to stand at room temperature for 30 minutes, then cured at 100° C. for 15 minutes.

(c) Coupling of FMOC-15-ATOM-PEG to a Carboxy Chip

The derivatized slide from above is immersed into a solution of N-(t-butoxycarbonyl)ethylenediamine (Fluka Chemic, Switzerland) (0.1M) and 1,3-diisopropylcarbodiimide (0.1M) in DMF for 2 hours at room temperature. The slide is extensively washed with DMF, $CH_2Cl_2$, and MeOH and then air-dried. Residual carboxylic acid groups are blocked by incubating the slide with excess diazomethane in ether for 10 minutes at room temperature. After washing the slide with $CH_2Cl_2$, the BOC group is removed by immersing the slide in 50% TFA/$CH_2Cl_2$ for 30 minutes, and washed again with $CH_2Cl_2$. The slide is then immersed in a 5% solution of DIEA/DMF to neutralize the TFA salts and is further derivatized by immersion in a 0.1M solution of FMOC-15-ATOM-PEG (See Example 4) in DMF activated as its OBt ester via BOP/HOBt. After standing at room temperature for 2 hours, the slide is washed with DMF, $CH_2Cl_2$, and MeOH and then air dried.

EXAMPLE 6

This example illustrate the preparation of polymer-coated surfaces for solid phase synthesis.

(a) Preparation of 3-(Triethoxysilyl)propylacrylamide

To a solution of acryloyl chloride (8.5 mL, 105 mmol) in dry dichloromethane (250 mL) cooled to 0° C. was added dropwise a mixture of 3-aminopropyltriethoxysilane (23.5 mL, 100 mmol) and triethylamine (13.9 mL, 100 mmol) in dichloromethane (50 mL). After completion of addition the reaction mixture was stirred for 30 min, then filtered. The filtrate was concentrated to an oil, diluted with hexane (100 mL) and filtered. The resulting filtrate was concentrated to oil and distilled in vacuo. The product was obtained as a viscous liquid (21.2 g, 77%), b.p. 142–145/1 mm Hg.

(b) Preparation of (2-Aminoethyl)acrylamide Hydrochloride

To a solution of acryloyl chloride (2.25 mL, 65 mmol) in ethyl ether (200 mL) cooled to 0° C. was added ethylenediamine (4.2 mL, 63 mmol) in ether (25 mL) slowly with vigorous stirring. After the addition was completed, the product (2-aminoethyl)acrylamide hydrochloride was removed by filtration, washed with ether on the filter and dried to provide 8.2 g (87%) of the product.

(c) Preparation of Polymer-coated Glass Supports

Chemically cleaned glass was treated with neat chlorotrimethylsilane for 1–2 min, allowed to dry and washed with distilled water. After drying by nitrogen stream, the glass was used as hydrophobic cover glass.

The second glass plate of the same surface quality was treated for 15–20 min with 5–10% solution of 3-(triethoxysilyl)propylacrylamide in 95% alcohol. After this it was washed intensively with alcohol and dried by nitrogen stream. This glass was used further as bound glass. An aqueous monomer solution was prepared providing 0.8M N,N-dimethylacrylamide, 0.1M (2-aminoethyl) acrylamide, 16 mM methylenebisacrylamide and a small amount of ammonium persulfate solution. Before using, the mixture was filtered.

Two 13 mm (or other size) spacer strips were put on sides of cover glass. The monomer solution was activated by a trace amount of TEMED, and the polymerizing mixture was then put on the surface of cover glass between spacers and covered with bound glass. The glass "sandwich" was fixed with two clamps and kept for 15–20 min. After completion of polymerization, the glass "sandwich" was rinsed with distilled water and carefully disconnected. The resulting gel chip was washed with distilled water for 5–10 hours to remove any low molecular weight compounds, then with 0.1M KOH for 5 min, and with distilled water for 5 min. After washing with alcohol, the chips were dried.

EXAMPLE 7

This example illustrates a method for the attachment of a thin film of crosslinked amino-functionalized acrylamide copolymer to a glass support for use in solid-phase oligo-nucleotide synthesis. In this example, acrylamide groups are attached to the glass support using acrylamidopropyltri-ethoxysilane. A synthesis initiation site is introduced into the polymer backbone by polymerizing N-(2-aminoethyl) acrylamide in an aqueous solution of dimethylacrylamide. Other monomers can also be used (e.g., N-(2-hydroxyethyl)-acrylamide), and oligonucleotide synthesis proceeds smoothly with either amino- or hydroxyl-functionalized supports. Polymerization was carried out between the acrylamide-derivatized substrate and another glass plate which was prepared so as not to adhere to the polymer film afterwards (see Example 6).

In this case, the thickness of the resulting gel is equivalent to that of the spacers used (13 or 50 microns).

After drying, arrays of oligonucleotide probes were synthesized on the films using standard VLSIPS™ procedures with no significant modifications. Stepwise coupling efficiencies were determined by fluorescence staining and HPLC methods, and hybridization to oligonucleotide targets was compared with arrays on standard VLSIPS™ glass substrates.

Synthesis of d(T)16 on 50 mm polydimethylacrylamide film using DMT chemistry showed high efficiency from third to 16th base according to DMT cation photometry. An overall yield of 88% was observed, corresponding to a stepwise yield of >99%.

The capacity of the 50 µm PDM chip based on first DMT is 90 nmol on a 1-inch×1-inch square. This corresponds to 6 mM concentration. Six percent of total amines were involved in oligonucleotide synthesis.

EXAMPLE 8

This example illustrates the preparation of carboxymeth-yldextran.

Dextran T500 (1.5 g having a molecular weight 500,000, available from Pharmacia Biotech, Inc., Piscataway, N.J., USA) was dissolved in aqueous base (2N NaOH) and bromoacetic acid (1.0 g) was added. After 3 hr at room temperature, an additional 1.0 g of bromoacetic acid was added and the mixture was kept at room temperature for 24 hr. The mixture was then dialyzed against distilled water for 24 hr, during which time the water was changed several times. Following dialysis, the aqueous solution was lyophilized to provide carboxymethyldextran as a solid (1.9 g, corresponding to approximately 24% of all secondary hydroxyls being carboxymethylated).

EXAMPLE 9

This example illustrates the coupling of carboxymethyl-dextran to a modified solid support.

Carboxymethyldextran (CM-dextran, 100 mg) was dissolved in 1 mL of 50 mM NaOAc buffer (pH 5.0). 1-Ethyl-3-(3-dimethylaminopropyl)carbodiimide (EDAC, 5 mg) was added and the mixture was contacted with a glass coverslip which had previously been modified with amino-propyltriethoxysilane (according to the standard process above). The reaction was allowed to proceed overnight to produce a dextran-coated surface which exhibited a contact angle of 5°–10°. Subsequent coupling with either FMOC-Lys or FMOC-diaminopropane (100 mM) using 100 mM DCC/HOBt in DMF for two hours with 200 mM triethylamine provided the desired coupled products. Deprotection of the Lys or aminopropyl groups was accomplished using 20% piperidine for 20 minutes at room temperature. The resulting dextran-modified surfaces can be used in VLSIPS™ synthesis without further modification.

X. Conclusion

All publications, patents and patent applications mentioned in this specification are herein incorporated by reference into the specification to the same extent as if each individual publication, patent or patent application was specifically and individually indicated to be incorporated herein by reference.

The above description is illustrative and not restrictive. Many variations of the invention will become apparent to those of skill in the art upon review of this disclosure. Merely by way of example a variety of substrates, polymers, linking groups, synthesis initiation sites, and other materials may be used without departing from the scope of the invention. The scope of the invention should, therefore, be determined not with reference to the above description, but instead should be determined with reference to the appended claims along with their full scope of equivalents.

What is claimed is:

1. A method for affixing functional sites to the surface of a solid substrate, comprising:
   (a) contacting said solid substrate with a derivatizaton reagent, said reagent having a substrate attaching group and a reactive site, to covalently bind said substrate attaching group to said substrate and thereby form a derivatized substrate having reactive sites; and
   (b) contacting said derivatized substrate with a mixture comprising linking molecules and diluent molecules, each of said linking molecules and diluent molecules having reactive groups capable of covalently binding to said reactive sites and said linking molecules alone further having a functional site for synthesis initiation, wherein said linking molecules and said diluent molecules are different and have different reactive properties and the ratio of said linking molecules to said diluent molecules in said mixture is selected to control the functional site density on said surface, to thereby bind said linking molecules and said diluent molecules to said substrate in accordance with said ratio.

2. A method in accordance with claim 1, wherein said substrate attaching group is a member selected from the group consisting of a trialkoxysilyl radical and a trichlorosilyl radical.

3. A method in accordance with claim 1, wherein said reactive site is a member selected from the group consisting of amino, hydroxyl, carboxylic acid, thiol, ester, amide, isocyanate and isothiocyanate.

4. A method in accordance with claim 1, wherein said derivatization reagent is an aminoalkyltrialkoxysilane.

5. A method in accordance with claim 1, wherein said functional site is a member selected from the group consisting of amino, hydroxyl, carboxylic acid, thiol, ester, amide, isocyanate and isothiocyanate.

6. A method in accordance with claim 1, wherein said diluent molecules are protected amino acids.

7. A method in accordance with claim 1, wherein said diluent molecules are members selected from the group consisting of protected glycine, protected serine and protected lysine, protected glutamic acid, protected aspartic acid, protected ornithine and protected phenylalanine.

8. A method in accordance with claim 1, wherein said ratio is from about 1:2 to about 1:200.

* * * * *